(12) United States Patent
Shinozaki et al.

(10) Patent No.: US 6,470,760 B2
(45) Date of Patent: *Oct. 29, 2002

(54) METHOD AND APPARATUS FOR AUTOMATICALLY ANALYZING TRACE SUBSTANCE

(75) Inventors: Tsutomu Shinozaki; Masaru Shimobayashi; Yuuichi Satou, all of Tokyo (JP)

(73) Assignee: NEC Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/343,656

(22) Filed: Jun. 29, 1999

(65) Prior Publication Data

US 2002/0121148 A1 Sep. 5, 2002

(30) Foreign Application Priority Data

Jun. 29, 1998 (JP) .......................................... 10-182651
Mar. 25, 1999 (JP) .......................................... 11-081067

(51) Int. Cl.[7] ............................ G01N 1/40; G01N 1/34; G01N 1/26; G01N 35/00; G01N 30/08
(52) U.S. Cl. ................... 73/863.33; 73/23.36; 73/23.41; 422/88; 422/89; 422/93; 436/50; 436/178; 436/181
(58) Field of Search ........................ 73/863.33, 864.81, 73/23.36, 23.41; 436/50, 174, 178, 181; 422/83, 88, 89, 93

(56) References Cited

U.S. PATENT DOCUMENTS

| | | | | |
|---|---|---|---|---|
| 3,483,731 A | * | 12/1969 | Sanford et al. ............. | 73/23.35 |
| 3,757,583 A | * | 9/1973 | Ludewig, Jr. ............. | 73/863.33 |
| 3,921,457 A | * | 11/1975 | Barnes, Jr. et al. ...... | 73/863.33 |
| 4,090,392 A | * | 5/1978 | Smith et al. .......... | 73/863.33 X |
| 4,386,534 A | * | 6/1983 | Englund et al. ..... | 73/863.33 X |
| 4,399,688 A | * | 8/1983 | Dennis ................ | 73/864.81 X |
| 4,779,466 A | * | 10/1988 | Ramsner ................... | 73/863.33 |
| 5,012,845 A | * | 5/1991 | Averette .............. | 73/864.84 X |
| 5,057,437 A | * | 10/1991 | Binder ................... | 436/178 X |
| 5,162,652 A | * | 11/1992 | Cohen et al. ........ | 73/863.33 X |
| 5,357,781 A | * | 10/1994 | Tikijian ...................... | 73/19.1 |
| 5,492,831 A | * | 2/1996 | Ranger ........................ | 436/50 |
| 5,661,224 A | * | 8/1997 | Walsh ........................ | 73/1.03 |
| 5,714,676 A | | 2/1998 | Hase .......................... | 73/23.41 |
| 6,125,710 A | * | 10/2000 | Sharp ..................... | 73/863.33 |
| 6,280,688 B1 | * | 8/2001 | Motz ......................... | 422/68.1 |
| 6,344,172 B1 | * | 2/2002 | Ateyan et al. ................. | 422/70 |

FOREIGN PATENT DOCUMENTS

| | | | | |
|---|---|---|---|---|
| EP | 91928 B1 | * | 2/1986 | .......... G01N/30/00 |
| EP | 249932 A2 | * | 12/1987 | ................. 530/413 |
| EP | 579 952 A1 | * | 6/1997 | ............ G01N/1/26 |

(List continued on next page.)

Primary Examiner—Thomas P. Noland

(57) ABSTRACT

An apparatus for automatically analyzing a trace substance capable of automatic analysis of a trace substance in a short time with high accuracy is provided. This apparatus comprises (a) samplers for making samples each containing a desired substance at different sampling points, (b) concentrators for concentrating the substance contained in the samples to thereby produce concentrated samples, (c) a quantitative analyzer for analyzing quantitatively the substance contained in the concentrated samples, and (d) a controller for controlling the samplers, the concentrators and the analyzer to cause automatically operations of the samplers, the concentrators, and the analyzer repeatedly at specific intervals of time. Each of the concentrators receives alternatively the samples from at least two of the samplers. The analyzer receives alternatively the concentrated samples from the concentrators. Preferably, the desired substance is gaseous and each of the concentrators has a diffusion scrubber and a concentration column. A cleaner for cleaning the samplers by supplying a purging gas into the samplers may be additionally provided.

14 Claims, 16 Drawing Sheets

FOREIGN PATENT DOCUMENTS

| | | | | |
|---|---|---|---|---|
| EP | 739 483 B1 | * | 9/1998 | G01N/30/12 |
| JP | 54-20789 | * | 2/1979 | 73/863.33 |
| JP | 64-41858 | * | 2/1989 | 73/30.01 |
| JP | 7-5160 | * | 1/1995 | G01N/30/46 |
| JP | 8-54380 A | | 2/1996 | |
| JP | 9-101293 A | | 4/1997 | |
| JP | 9-196828 | | 7/1997 | |
| JP | 9-318609 | | 12/1997 | |
| JP | 10-090241 | | 4/1998 | |

* cited by examiner

METHOD AND APPARATUS FOR AUTOMATICALLY ANALYZING TRACE SUBSTANCE

BACKGROUND OF THE INVENTION

1. Field of the Invention

The present invention relates to a method and an apparatus for automatically analyzing a trace substance, and more Particularly, to a method and an apparatus for automatically analyzing a desired gaseous substance or substances existing in an atmosphere, which are preferably applied to monitoring gaseous contaminants existing in a clean room used in the field of semiconductor device fabrication.

2. Description of the Prior Art

A trace of gaseous contaminant remaining in a clean room atmosphere tends to increasingly cause failures or defects in next-generation semiconductor devices during their fabrication process steps. To stabilize the prosecution of the mass-production processes of the next-generation semiconductor devices, usually, suitable dust/chemical filters are used for removing dusts and chemicals existing in the air in the clean room. However, there is a possibility that contamination accidents occur due to supplied source materials for fabrication processes and that the dust/chemical filters may be damaged or broken due to contaminants. Thus, it is required to automatically and continuously measure and monitor contaminants existing in the air in a clean room.

In a prior-art multi-point measuring method for measuring trace contaminants at different positions in a clean room, desired gaseous contaminants are sampled from the air and then, concentrated to specific concentrations corresponding to the lower limit of an analytical apparatus or instrument by using the impinger method while taking a lot of time, thereby analyzing and quantitative analyzing the concentrated contaminants. However, there is a problem that the measuring interval of time is too long and the total amount of the contaminants at the measuring positions is unable to be determined, and that an outbreak of a high-concentration contaminant is unable to be well-treated.

On the other hand, there is a known prior-art multi-point analyzing method for automatically analyzing ammonia existing in a clean room atmosphere using a diffusion scrubber. FIGS. 1 and 2 show prior-art multi-point ammonia analytical apparatuses that perform this analyzing method, which are disclosed in the Japanese Non-Examined Patent Publication No. 8-54380 published in June 1994 and its corresponding U.S. Pat. No. 5,714,676 issued on Feb. 3, 1998.

In FIG. 1, the prior-art multi-point ammonia analytical apparatus is comprised of a sampler 1100, a concentrator 1200, and an analyzer 1300. The sampler 1100 has a switch valve 601 with ten inlets connected respectively with ten sampling points P1 to P10 located in the clean room, and a diffusion scrubber 602 connected to an outlet of the valve 601. The concentrator 1200 includes a concentration column 604 of an ion chromatograph 603. The analyzer 1300 includes a separation column 605, a suppressor 606, and an electrical conductivity meter 607 of the ion chromatograph 603. A controller 608 controls the whole operation of the sampler 1100, the concentrator 1200, and the analyzer 1300.

With the prior-art analytical apparatus of FIG. 1, the total measuring time $T_{total}$ for all the sampling points P1 to P10 is expressed as the following equation (1), where n is the number of the sampling points, and $T_{pt}$, $T_r$, $T_s$, and $T_{sa}$ are the times for the pre-treatment operation, the rinsing operation, the sampling operation, and the separation/analyzing operation, respectively.

$$T_{total} = n \times (T_{pt} + T_r + T_s + T_{sa}) \tag{1}$$

The schedule of the individual operations for the sampling points P1 to P10 is shown in FIG. 2. Specifically, at first, the pre-treatment and sampling operations are successively carried out for the sampling point P1 and then, the rinsing and separation/analysis operations for the same point P1 are successively carried out. Next, the same time schedule is successively repeated for each of the points P2 to P10.

In the prior-art analytical apparatus of FIG. 1, the switch valve 601 of the sampler 1100 assigns alternately one of the sampling points P1 to P10 to the diffusion scrubber 602. Thus, there is a problem that the total measuring time $T_{total}$ for all the sampling points P1 to P10 is very long.

For example, if the time $T_{pt}$ for the pre-treatment operation is 25 minutes, the time $T_r$ for the rinsing operation is 0.5 minute, the time $T_s$ for the sampling operation is 7.5 minutes, and the time $T_{sa}$ for the separating/analyzing operation is 8 minutes, the total time $T_{total}$ is 410 minutes.

The prior-art multi-point ammonia analytical apparatus shown in FIG. 3 is comprised of a sampler 2100, a concentrator 2200, and an analyzer 2300.

The sampler 2100 has a switch valve 701a having five inlets connected respectively with five sampling points P1 to P5, a diffusion scrubber 702a connected to an outlet of the valve 701a, a switch valve 701b having five inlets connected respectively with five sampling points P6 to P10, and a diffusion scrubber 702b connected to an outlet of the valve 701b.

The concentrator 2200 is comprised of a concentration column 704 of an ion chromatograph 703. The analyzer 2300 is comprised of a separation column 705, a suppressor 706, and an electrical conductivity meter 707 of the ion chromatograph 703.

A controller 708 controls the whole operation of the sampler 2100, the concentrator 2200, and the analyzer 2300.

With the prior-art analytical apparatus of FIG. 3, the controller 708 controls so that one of the valves 701a and 701b is used for the pre-treatment operation while the other of the valves 701a and 701b is used for the rinsing, sampling, and separation/analysis operations. The schedule of the individual operations for the sampling points P1 to P10 is shown in FIG. 4.

Thus, the total measuring time $T_{total}$ for all the sampling points P1 to P10 is expressed as the following equation (2) under the condition that the following inequality (3) is established.

$$T_{total} = n \times (T_r + T_s + T_{sa}) \tag{2}$$

$$T_{pt} \geq T_r + T_s + T_{sa} \tag{3}$$

The inequality (3) means that the time $T_{pt}$ for the pre-treatment operation is equal to or greater than the sum of the times for the rinsing, sampling, and separation/analysis operations, i.e., $(T_r + T_s + T_{sa})$.

In the prior-art analytical apparatus of FIG. 3, for example, if the time $T_{pt}$ for the pre-treatment operation is 25 minutes, the time $T_r$ for the rinsing operation is 0.5 minute, the time $T_s$ for the sampling operation is 7.5 minutes, and the time $T_{sa}$ for the separating/analyzing operation is 8 minutes, the total time $T_{total}$ is 185 minutes. Thus, there is a same problem that the total time measuring time $T_{total}$ for all the sampling points P1 to P10 is still long.

Moreover, gaseous ammonia tends to remain in the sampler 1100 or 2100 and the concentrator 1200 or 2200 after a sampled air with high-concentration ammonia is measured. The remaining ammonia or residue in a prior measuring step affects badly a subsequent measuring step. This is called the "memory effect" of the residue.

In particular, when an organic substance such as monoethanolamine is analyzed and measured in the above-described prior-art apparatuses of FIGS. 1 and 3, the organic substance is extremely easy to remain in the inside of the apparatuses. Thus, correct measurement is unable or very difficult to be carried out.

SUMMARY OF THE INVENTION

Accordingly, a general object of the present invention to provide a method and an apparatus for automatically analyzing a trace substance capable of automatic analysis of a trace substance in a short time with high accuracy.

A specific object of the present invention to provide a method and an apparatus for automatically analyzing a trace substance that decreases the time for each cycle of measurement or analysis.

Another specific object of the present invention to provide a method and an apparatus for automatically analyzing a trace substance that simplifies the structure of the sampler.

Still another specific object of the present invention to provide a method and an apparatus for automatically analyzing a trace substance that suppress the memory effect due to a residue of the substance.

A further specific object of the present invention to provide a method and an apparatus for automatically analyzing a trace substance capable of monitoring the occurrence or outbreak of an abnormal concentration of the substance.

A still further specific object of the present invention to provide a method and an apparatus for automatically analyzing a trace substance capable of monitoring the cumulative sum of the substance in a specific period of time.

The above objects together with others not specifically mentioned will become clear to those skilled in the art from the following description.

According to a first aspect of the present invention, an apparatus for automatically analyzing a trace substance is provided, which is comprised of (a) samplers for making samples each containing a desired substance at different sampling points, (b) concentrators for concentrating the substance contained in the samples to thereby produce concentrated samples, (c) a quantitative analyzer for analyzing quantitatively the substance contained in the concentrated samples, and (d) a controller for controlling the samplers, the concentrators and the analyzer to cause automatically operations of the samplers, the concentrators, and the analyzer repeatedly at specific intervals of time.

Each of the concentrators receives alternatively the samples from at least two ones of the samplers.

The analyzer receives alternatively the concentrated samples from the concentrators.

With the apparatus for automatically analyzing a trace substance according to the first aspect of the present invention, each of the concentrators receives alternatively the samples from at least two ones of the samplers, and the analyzer receives alternatively the concentrated samples from the concentrators. Therefore, the analyzer can receive alternatively the concentrated samples from the concentrators without waiting or idle time under the control of the controller. Accordingly, the time for each cycle of measurement or analysis can be decreased.

Also, since each of the samplers makes the corresponding sample containing the desired substance at the different sampling points, each of the samplers can make the samples by using common sampling tubes connected to the respective sampling points. Thus, the structure of the samplers is simplified.

Moreover, since the analyzer receives alternatively the concentrated samples from the concentrators, an unused one or ones of the concentrators and its relating samplers can be cleaned or rinsed while the analyzing operation of the used one of the concentrators is performed. Thus, the memory effect due to a residue of the substance can be suppressed.

As a result, the apparatus according to the first aspect of the present invention has an advantage that automatic analysis of a trace substance can be realized in a short time with high accuracy.

In a preferred embodiment of the apparatus according to the first aspect, the desired substance is gaseous and each of the concentrators has a diffusion scrubber and a concentration column.

In another preferred embodiment of the apparatus according to the first aspect, the desired substance is gaseous and each of the concentrators has four diffusion scrubbers and two concentration columns.

In still another preferred embodiment of the apparatus according to the first aspect, the analyzer has a function of ion chromatograph.

In a further preferred embodiment of the apparatus according to the first aspect, the controller has a function of monitoring an outbreak of a high-concentration state of the substance. In this embodiment, there is an additional advantage that the occurrence or outbreak of an abnormal concentration of the substance can be monitored.

In a still further preferred embodiment of the apparatus according to the first aspect, the controller has a function of calculating a cumulative sum of the substance in a specific period of time. In this embodiment, there is an additional advantage that the cumulative sum of the substance in a specific period of time can be monitored.

In a more further preferred embodiment of the apparatus according to the first aspect, a cleaner for cleaning the samplers by supplying a purging gas into the samplers is additionally provided.

It is preferred that the cleaner is comprised of a container for containing the purging gas, and a valve for selecting one of flow paths for the samples and for the purge gas.

Each of the diffusion scrubbers may have the cleaner.

According to a second aspect of the present invention, another apparatus for automatically analyzing a trace substance is provided, which is comprised of (a) a sampler for making a sample containing a desired substance at a sampling point, the sampler including a diffusion scrubber, (b) a concentrator for concentrating the substance contained in the sample to thereby produce a concentrated sample, the concentrator including a concentration column, (c) a quantitative analyzer for analyzing quantitatively the substance contained in the concentrated sample, (d) a cleaner for cleaning the sampler by using a purging gas, and (e) a controller for controlling the sampler, the concentrator, the analyzer, and the cleaner to cause automatically operations of the sampler, the concentrator, the analyzer, and the cleaner repeatedly at specific intervals of time.

With the apparatus for automatically analyzing a trace substance according to the second aspect of the present invention, because of the cleaner being provided, the memory effect due to a residue of the substance can be suppressed.

In a preferred embodiment of the apparatus according to the second aspect, the cleaner is comprised of a tank for storing a purging gas, and a valve for connecting the tank with the diffusion scrubber of the sampler.

In another preferred embodiment of the apparatus according to the second aspect, an additional sampler for making an additional sample containing the desired substance at a sampling point, the additional sampler including a diffusion scrubber. The two diffusion scrubbers of the samplers are alternately connected to the concentrator. The cleaners are designed for cleaning the two samplers.

According to a third aspect of the present invention, a method for automatically analyzing a trace substance is provided, which is performed in the apparatus according to the first aspect.

This method includes a "pre-treatment operation" for supplying an absorbing liquid to at least one of the samplers to suppress the effect of a residue of the substance generated in a prior measurement step, a "rinsing operation" for rinsing an eluting liquid remaining in one of the concentrators, a "sampling operation" for making the samples by the samplers and for making the concentrated samples by the concentrators, and a "separation/analysis operation" for separating the substance from the samples and for quantitatively analyzing the separated substance.

Moreover, a time of the "separation/analysis operation" is equal to the sum of a time of the "rinsing operation" and a time of the "sampling operation".

With the method according to the third aspect of the present invention, the total analyzing time is minimized.

According to a fourth aspect of the present invention, another method for automatically analyzing a trace substance is provided, which is performed in the apparatus according to the first aspect equipped with the cleaner.

This method includes a "cleaning operation" for cleaning the samplers using the purging gas, a "pre-treatment operation" for supplying an absorbing liquid to at least one of the samplers to suppress the effect of a residue of the substance generated in a prior measurement step, a "rinsing operation" for rinsing an eluting liquid remaining in one of the concentrators, a "sampling operation" for making the samples by the samplers and for making the concentrated samples by the concentrators, and a "separation/analysis operation" for separating the substance from the samples and for quantitatively analyzing the separated substance.

Moreover, a time of the "separation/analysis operation" is equal to the sum of a time of the "cleaning operation" and a time of the "pre-treatment operation".

With the method according to the fourth aspect of the present invention, the total analyzing time is minimized.

According to a fifth aspect of the present invention, still another method for automatically analyzing a trace substance is provided, which is performed in the apparatus according to the second aspect.

This method includes a "cleaning operation" for cleaning the sampler using the purging gas, a "pre-treatment operation" for supplying an absorbing liquid to the sampler to suppress the effect of a residue of the substance generated in a prior measurement step, a "rinsing operation" for rinsing an eluting liquid remaining in the concentrator, a "sampling operation" for making the sample by the sampler and for making the concentrated sample by the concentrator, and a "separation/analysis operation" for separating the substance from the sample and for quantitatively analyzing the separated substance.

Moreover, a time of the "separation/analysis operation" is equal to the sum of a time of the "cleaning operation" and a time of the "pre-treatment operation".

With the method according to the fifth aspect of the present invention, the total analyzing time is minimized.

BRIEF DESCRIPTION OF THE DRAWINGS

In order that the present invention may be readily carried into effect, it will now be described with reference to the accompanying drawings.

DETAILED DESCRIPTION OF THE PREFERRED EMBODIMENTS

Figure 1:
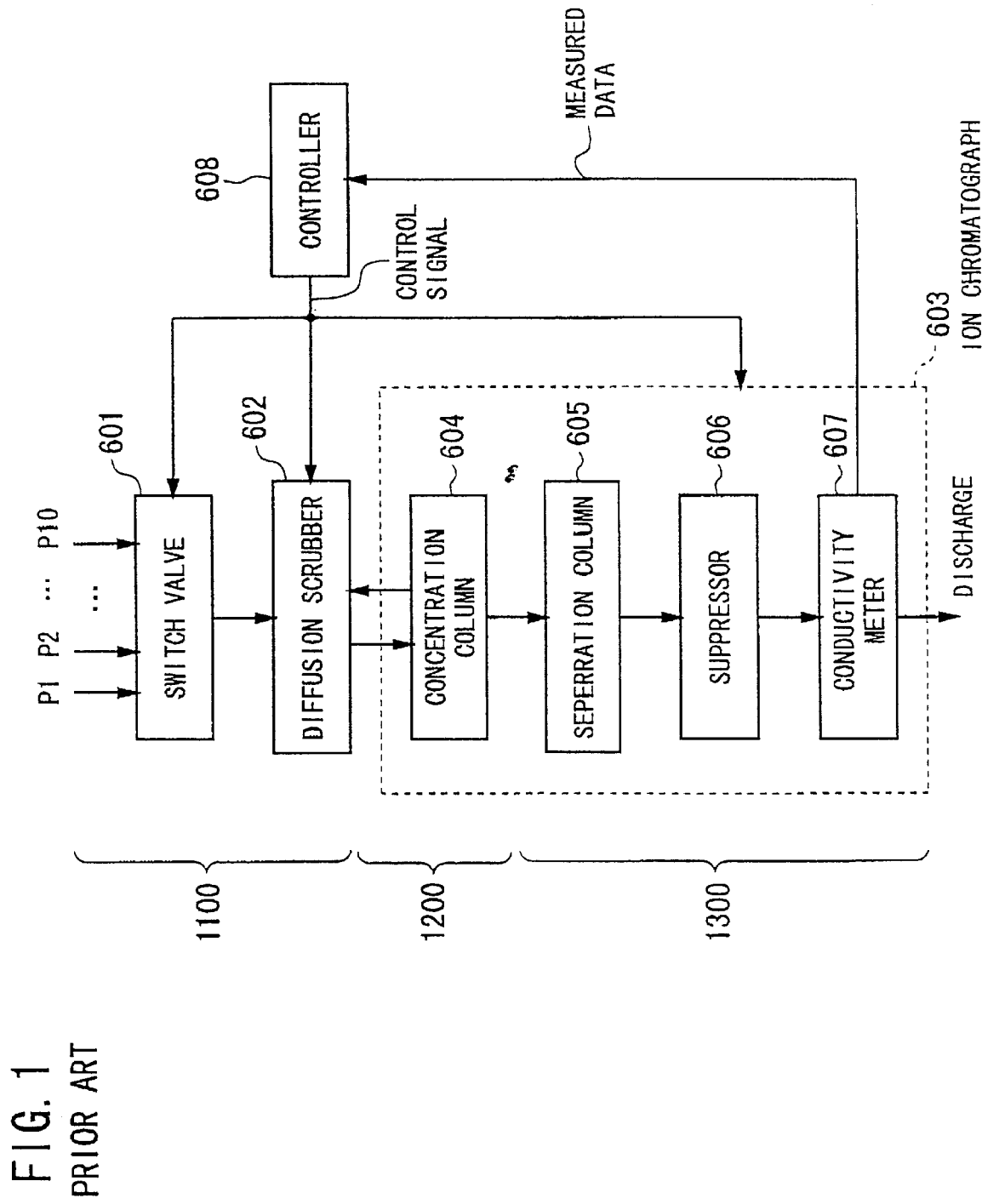
FIG. 1 is a schematic block diagram showing the configuration of a prior-art apparatus for automatically analyzing a trace substance.
Figure 2:
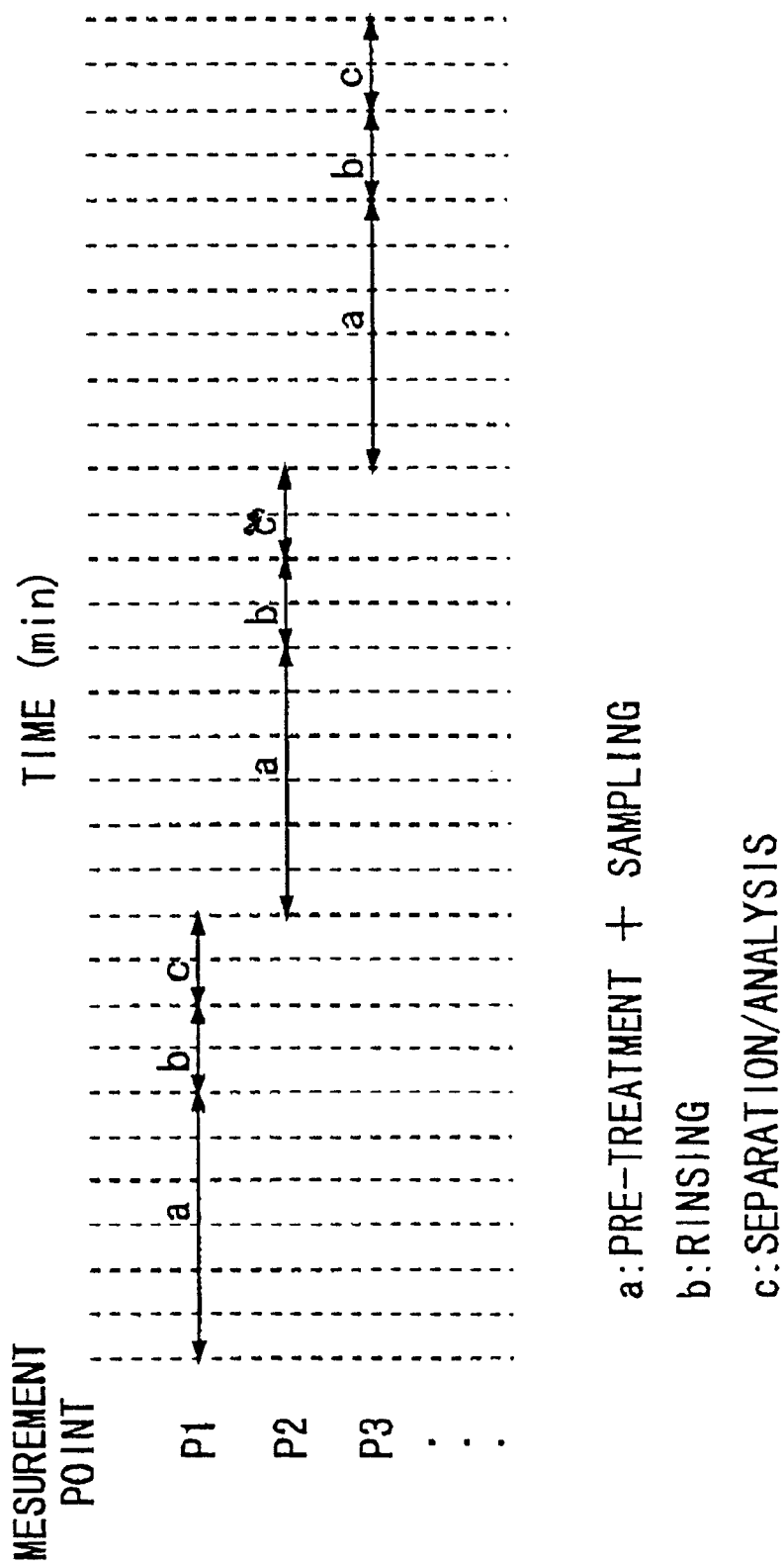
FIG. 2 is a diagram showing the schedule of the individual operations for the ten sampling points in the prior-art apparatus of FIG. 1.

Preferred embodiments of the present invention will be described in detail below while referring to the drawings attached.

FIRST EMBODIMENT (Basic Configuration)

Figure 6:
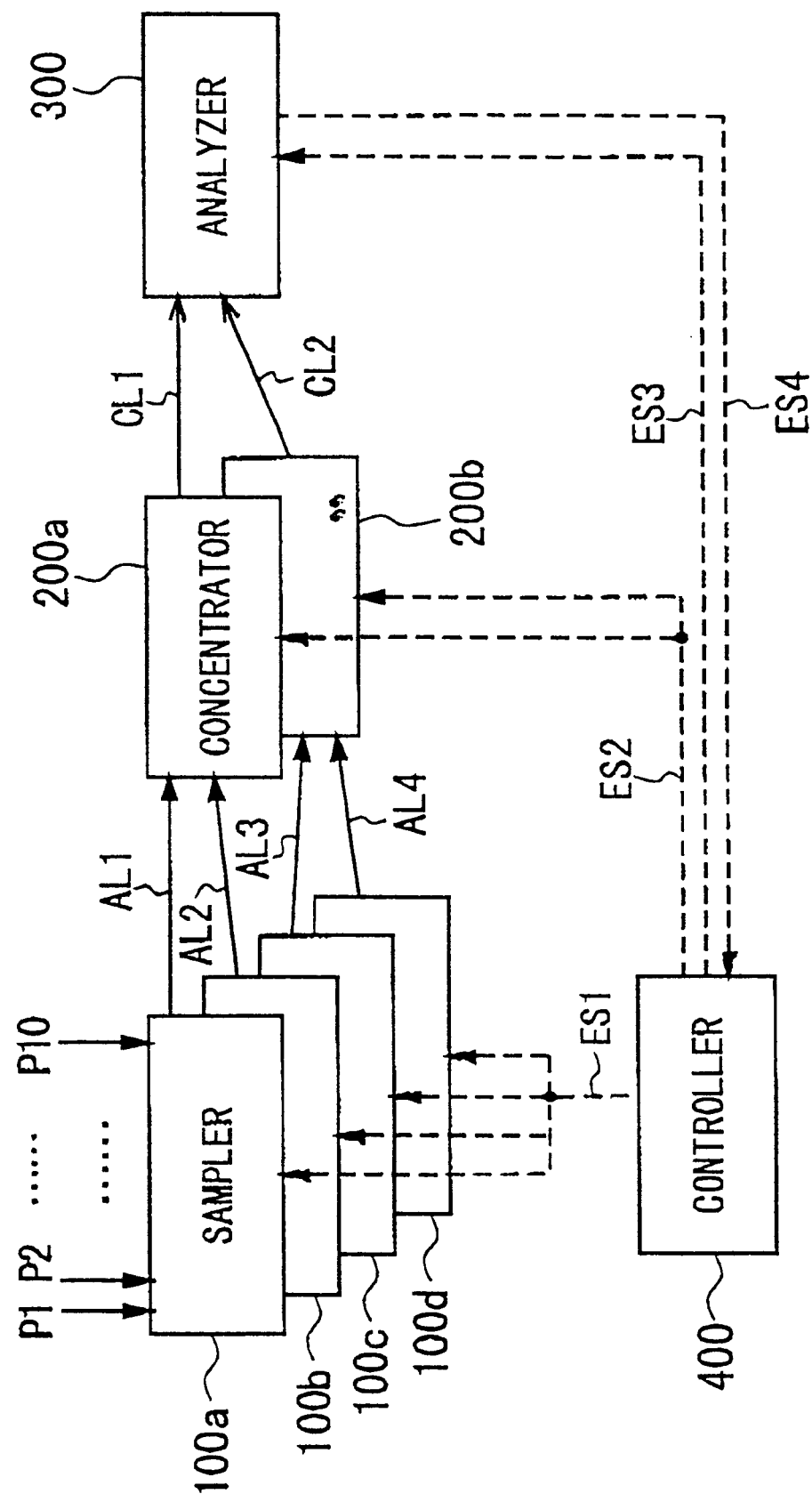
FIG. 6 is a schematic block diagram showing the configuration of an apparatus for automatically analyzing a trace substance according to a first embodiment of the present invention.

An apparatus for automatically analyzing a trace substance according to a first embodiment of the present invention has a basic configuration shown in FIG. 6. Specifically, the apparatus is comprised of four samplers 100a, 100b, 100c, and 100d, two concentrators 200a and 200b, an analyzer 300, and a controller 400.

Each of the samplers 100a, 100b, 100c, and 100d, which is communicated with ten sampling points P1, P2, P3, P4, P5, P6, P7, P8, P9, and P10 set at different locations in a clean room for semiconductor device fabrication, samples the air at any one of the ten points P1 to P10. The sampled air contains trace substances such as ammonia existing in the clean room. The trace substances in the sampled air are then absorbed into an absorbing liquid in the corresponding sampler, making a sample of the trace substances. The samples of the trace substances in the absorbing liquid, which are respectively emitted by the samplers 100a, 100b, 100c, and 100d, are termed AL1, AL2, AL3, and AL4, respectively.

The concentrator 200a is connected to the two samplers 100a and 100b and the concentrator 200b is connected to the two samplers 100c and 100d. This configuration is to enable a "pre-treatment operation" to be carried out for a sufficiently long time. The "pre-treatment operation" means an operation where the inside of a corresponding one of the four samplers 100a, 100b, 100c, and 100d is cleaned without any sampling operation.

The concentrator 200a receives the sample AL1 or AL2 of the trace substances emitted from the sampler 100a or 100b and then, concentrates the trace substances, producing a concentrated sample CL1 of the trace substances. The concentrated sample CL1 thus produced is sent to the analyzer 300. Similarly, the concentrator 200b receives the sample AL3 or AL4 of the trace substances emitted from the sampler 100c or 100d and then, concentrates the trace substances, producing a concentrated sample CL2 of the trace substances. The concentrated sample CL2 thus produced is sent to the analyzer 300.

The concentrators 200a and 200b are controlled by the controller 400 in such a way that any one of the concentrators 200a and 200b always sends the concentrated sample CL1 or CL2 to the analyzer 300. At the same time as this, the remaining one of the concentrators 200a and 200b, which does not send the concentrated sample to the analyzer 300, is subjected to a "rinsing operation" in which the inside of the corresponding one of the concentrators 200a and 200b is rinsed to remove the residue of the absorbing liquid (i.e., the trace substances), or to a "sampling operation" in which the trace substances in the air are sampled by a corresponding one of the samplers 100a, 100b, 100c, and 100d and the sampled substances absorbed into the absorbing liquid are concentrated in a corresponding one of the concentrators 200a and 200b.

The analyzer 300 is alternately connected to one of the two concentrators 200a and 200b. The analyzer 300 receives the concentrated samples CL1 or CL2 of the substances and then, analyzes quantitatively the same, thereby producing time-dependent concentration data of the desired substance or substances. Thus, the time-dependent concentration of the trace substances existing in the clean room is monitored.

The controller 400 controls the four samplers 100a, 100b, 100c, and 100d, the two concentrators 200a and 200b, and the analyzer 300, thereby repeating automatically the above-described "pre-treatment operation", "rinsing operation", and "sampling operation" at specific intervals of time. The reference characters ES1, ES2, and ES3 in FIG. 6 denote control signals for the samplers 100a, 100b, 100c, and 100d, the concentrators 200a and 200b, and the analyzer 300, respectively. The reference character ES4 in FIG. 6 denotes a data signal of the analyzed substances outputted from the analyzer 300.

Moreover, the controller 400 have the following functions. First, the controller 400 displays the time-dependent concentration data of the desired substance or substances and store the same in a suitable storage device. Second, when the concentration of the desired substance or substances existing in the clean room becomes drastically high at one of the sampling points P1 to P10 due do some cause, the controller 400 assigns a corresponding one of the four samplers 100a, 100b, 100c, and 100d to the necessitated sampling point, dedicating the assigned sampler to monitoring at the same sampling point. Third, the controller 400 calculates the total amount of the accumulated substance or substances in a specific period of time at each of the ten sampling points P1 to P10.

(Detailed Configuration)

Figure 7:
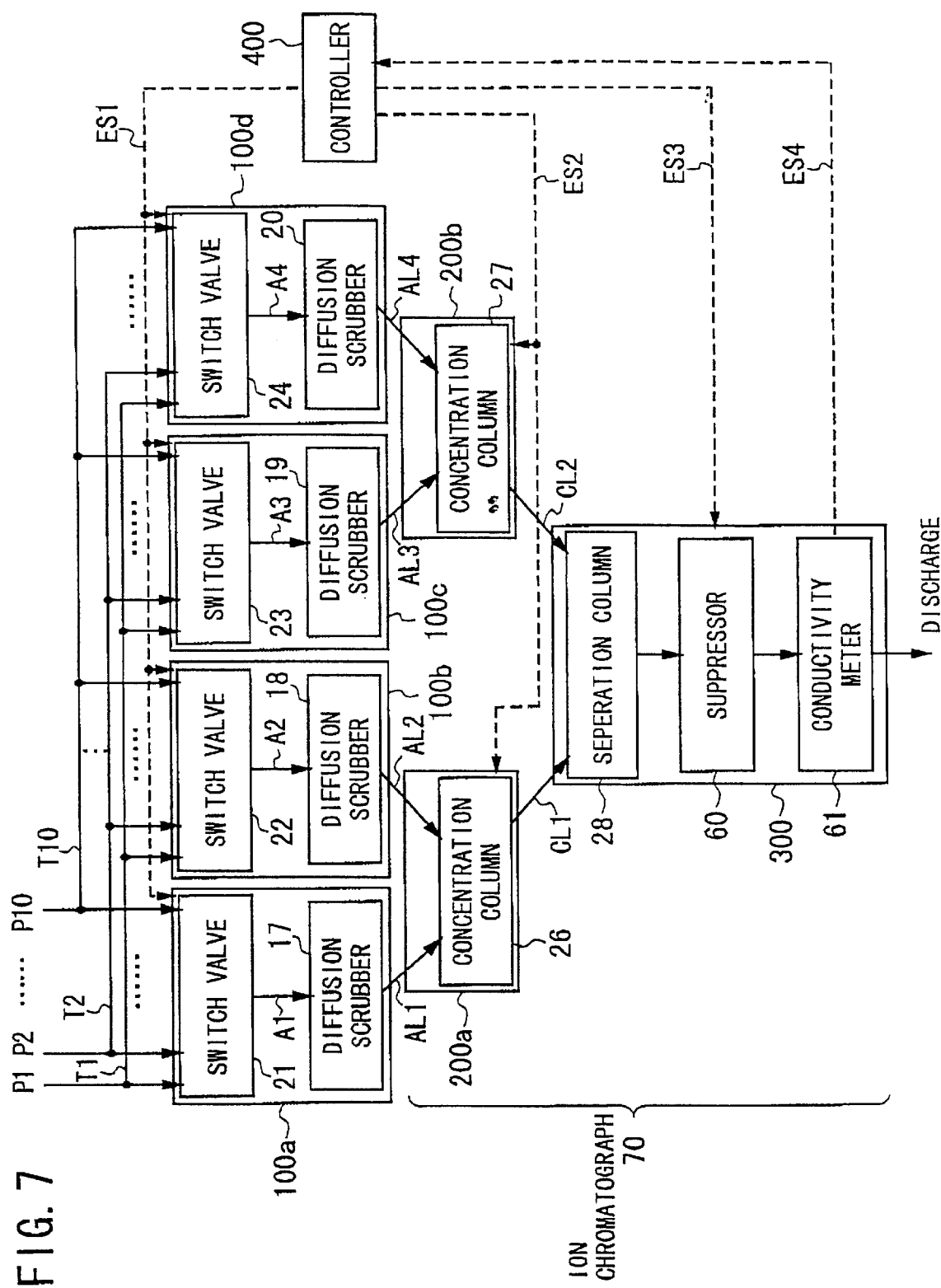
FIG. 7 is a schematic block diagram showing the detailed configuration of the apparatus according to the first embodiment of FIG. 6.

FIG. 7 shows the detailed configuration of the apparatus for automatically analyzing a trace substance according to the first embodiment of FIG. 6, in which the structural elements of each of the four samplers 100a, 100b, 100c, and 100d, the two concentrators 200a and 200b, and the analyzer 300 are illustrated This apparatus analyzes "gaseous ammonia" existing in the clean room as the desired trace substance. Thus, this apparatus may be termed a multipoint automatic-analyzing apparatus of ammonia.

As shown in FIG. 7, the sampler 100a includes a 10-way switch valve 21 and a diffusion scrubber 17. The valve 21 has ten inlets connected respectively to ten sampling tubes T1, T2, ..., T10 and one outlet connected to the scrubber 17. The ends of the tubes T1 to T10 are located at the sampling points P1 to P10, respectively. Because of the switching operation of the valve 21, the air existing at one of the sampling points P1 to P10 is alternately taken into the diffusion scrubber 17 through a corresponding one of the tubes T1 to T10 and the valve 21, thereby outputting a sample A1 of the air to the scrubber 17. The sample A1 of the air contains ammonia and other trace substances.

Similarly, the sampler 100b includes a 10-way switch valve 22 and a diffusion scrubber 18. The valve 22 has ten inlets connected respectively to the same sampling tubes T1 to T10 and one outlet connected to the scrubber 18. Because of the switching operation of the valve 22, the air existing at one of the sampling points P1 to P10 is alternately taken into the diffusion scrubber 18 through a corresponding one of the tubes T1 to T10 and the valve 22, thereby outputting a sample A2 of the air to the scrubber 18. The sample A2 of the air contains ammonia and other trace substances.

The sampler 100c includes a 10-way switch valve 23 and a diffusion scrubber 19. The valve 23 has ten inlets connected respectively to the same sampling tubes T1 to T10 and one outlet connected to the scrubber 19. Because of the switching operation of the valve 23, the air existing at one of the sampling points P1 to P10 is alternately taken into the diffusion scrubber 19 through a corresponding one of the tubes T1 to T10 and the valve 23, thereby outputting a sample A3 of the air to the scrubber 19. The sample A3 of the air contains ammonia and other trace substances.

The sampler 100d includes a 10-way switch valve 24 and a diffusion scrubber 20. The valve 24 has ten inlets connected respectively to the same sampling tubes T1 to T10 and one outlet connected to the scrubber 20. Because of the switching operation of the valve 24, the air existing at one of the sampling points P1 to P10 is alternately taken into the diffusion scrubber 20 through a corresponding one of the tubes T1 to T10 and the valve 24, thereby outputting a sample A4 of the air to the scrubber 20. The sample A4 of the air contains ammonia and other trace substances.

The switch valves 21, 22, 23, and 24 are controlled by the controller 400 in such a way as to be connected with four different ones of the sampling positions P1 to P10, respectively. Therefore, the air in the clean room is simultaneously sampled at four different sampling points, resulting in the sample airs A1, A2, A3, and A4 outputted from the valves 21, 22, 23, and 24, respectively.

Each of the diffusion scrubbers 17, 18, 19, 20 has the same configuration as that disclosed in the Japanese Non-Examined Patent Publication No. 8-54380. Specifically, each of the scrubbers 17, 18, 19, and 20 is comprised of an inner tube (not shown) and an outer tube (not shown) fixed coaxially to the inner tube. The inner tube includes a micro-porous membrane (not shown) allowing gaseous substances to penetrate through the membrane and preventing a liquid from penetrating through the same. An absorbing liquid or absorbent is moved through the space between the inner and outer tubes while the sample A1, A2, A3, or A4 of the air is moved through the inside of the inner tube. The gaseous substances (e.g., ammonia) contained in the sample A1, A2, A3, or A4 are absorbed into the absorbing liquid through the micro-porous membrane of the inner tube, thereby producing the sample AL1, AL2, AL3, or AL4 of the gaseous substances contained in the absorbing liquid.

The concentrator 200a is connected to the two diffusion scrubbers 17 and 18. The concentrator 200a is alternately supplied with one of the samples AL1 and AL2 of the substances from the scrubbers 17 and 18, thereby concentrating the trace substances contained in the samples AL1 and AL2. Thus, the concentrated sample CL1 of the trace substances is produced. The concentrated substances held in the concentrator 200a are dissolved in an eluting liquid and then, they are taken out of the concentrator 200a.

Similarly, the concentrator 200b is connected to the two diffusion scrubbers 19 and 20. The concentrator 200b is alternately supplied with one of the samples AL3 and AL4 of the trace substances from the scrubbers 19 and 20, thereby concentrating the trace substances contained in the samples AL3 and AL4. Thus, the concentrated sample CL2 of the trace substances is produced. The concentrated substances held in the concentrator 200b are dissolved in an eluting liquid and then, they are taken out of the concentrator 200b.

The concentrated samples CL1 and CL2 of the trace substances are alternately supplied to the analyzer 300. The analyzer 300 separates the concentrated substances in the sample CL1 or CL2 and quantitatively analyzes the separated substances thereby outputting the analyzed data ES4 to the controller 400.

The analyzer 300 and the two concentration columns 200a and 200b are part of an ion chromatograph 70. The analyzer 300 is comprised of a separation column 28, a suppressor 60, and an electrically conductivity meter 61. The separation column 28 separates specific cations such as ammonia ion from the sample CL1 or CL2 in the eluting liquid. The suppressor 60 decreases the electrical conductivity of the background of the sample CL1 or CL2 in the eluting liquid. The conductivity meter 61 measures the electrical conductivity of the sample CL1 or CL2 in the eluting liquid. The sample CL1 or CL2 in the eluting liquid is discharged after the separation and analyzing step is completed.

The analyzing apparatus shown in FIG. 7 repeats the cycle of four different operations, i.e., the "pre-treatment operation", the "rinsing operation", the "sampling operation", and the "separating/analyzing operation".

In the "pre-treatment operation", the absorbing liquid is circulated through the diffusion scrubbers 17, 18, 19, and 20 to suppress the effect of the residue occurred in a prior measurement step.

In the "rinsing operation", the eluting liquid remaining in the concentration columns 26 and 27 is rinsed with an absorbing liquid or pure water after the pre-treatment operation.

In the "sampling operation", the absorbing liquid is circulated between the diffusion scrubbers 17, 18, 19, and 20 and the concentration columns 26 and 27 to thereby cause the trace substances contained in the samples Al to A4 of the air to be absorbed in the absorbing liquid, resulting in the samples AL1 to AL4 of the trace substances. Then, the trace substances contained in the samples AL1 to AL4 are concentrated by the concentrators 200a and 200b, producing the samples CL1 or CL2 of the trace substances.

In the "separating/analyzing operation", the samples CL1 or CL2 of the trace substances is sent to the analyzer 300 by the eluting liquid. The trace substances in the sample CL1 or CL2 are dissolved in the eluting liquid. The analyzer 300 separates the substances in the eluting liquid and quantitatively analyze the same using the function of the ion chromatograph 70.

(Concrete Configuration)

Figure 8:
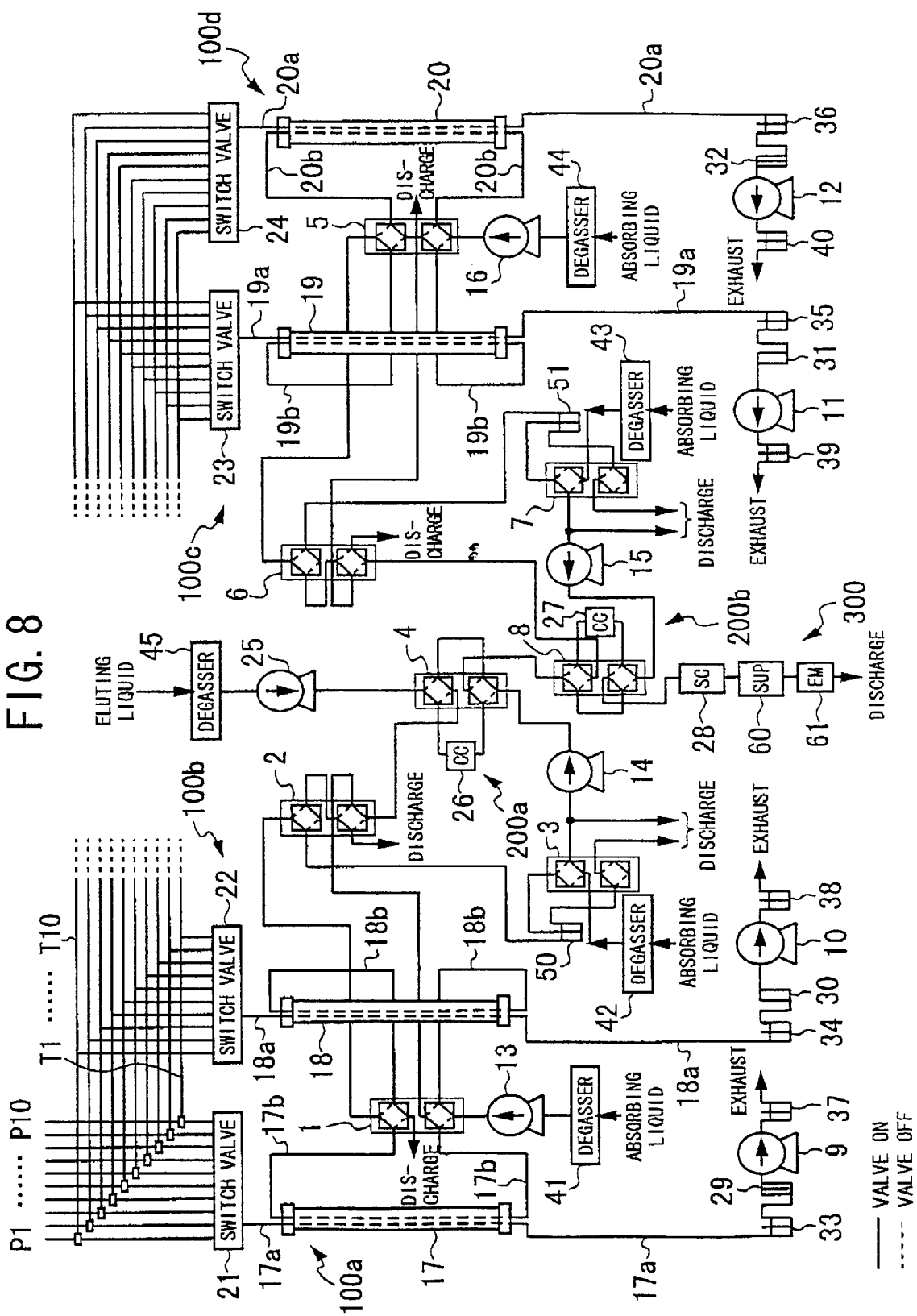
FIG. 8 is a schematic block diagram showing the concrete configuration of the apparatus according to the first embodiment of FIGS. 6 and 7.

FIG. 8 shows a concrete configuration of the analyzing apparatus according to the first embodiment of FIGS. 6 and 7, in which connecting tubes and pumps and relating elements are illustrated in detail.

(Samplers & Concentrators)

As shown in FIG. 8, each of the 10-way switch valves 21, 22, 23, and 24 of the samplers 100a, 100b, 100c, and 100d has the ten inlets communicated respectively with the ten sampling points P1 to P10. These valves 21, 22, 23, and 24 are controlled by the controller 400 so as not to collect the air from the same sampling points at the same time.

The diffusion scrubber 17 has an air path 17a through which the sampled air flows and a liquid path 17b through which the absorbing liquid flows. The air path 17a connects the outlet of the valve 21 to one end of a trap 33 through the diffusion scrubber 17. The air path 17a is further connected to an exhaust port of the apparatus through a mass flow controller (MFC) 29, a suction pump 9, and a trap 37. Two ends of the liquid path 17b are connected to two ports of an 8-port valve 1, respectively.

Similarly, the diffusion scrubber 18 has an air path 18a through which the sampled air flows and a liquid path 18b through which the absorbing liquid flows. The air path 18a connects the outlet of the valve 22 to one end of a trap 34 through the diffusion scrubber 18. The air path 18a is further connected to an exhaust port of the apparatus through a MFC 30, a suction pump 10, and a trap 38. Two ends of the liquid path 18b are connected to two other ports of the 8-port valve 1, respectively.

The diffusion scrubber 19 has an air path 19a through which the sampled air flows and a liquid path 19b through which the absorbing liquid flows. The air path 19a connects the outlet of the valve 23 to one end of a trap 35 through the diffusion scrubber 19. The air path 19a is further connected to an exhaust port of the apparatus through a MFC 31, a suction pump 11, and a trap 39. Two ends of the liquid path 19b are connected to two ports of an 8-port valve 5, respectively.

The diffusion scrubber 20 has an air path 20a through which the sampled air flows and a liquid path 20b through which the absorbing liquid flows. The air path 20a connects the outlet of the valve 24 to one end of a trap 36 through the diffusion scrubber 20. The air path 20a is further connected to an exhaust port of the apparatus through a MFC 32, a suction pump 12, and a trap 40. Two ends of the liquid path 20b are connected to two other ports of the 8-port valve 5, respectively.

The diffusion scrubbers 17, 18, 19, and 20 have an equal length of, for example, 80 cm. To ensure a desired sampling or collecting rate of the air in the clean room, the length is preferably 80 cm or longer. Although this length may be shorter than 80 cm, there is a possibility that the measured values of the substances contain significant errors.

The traps 33, 34, 35, and 36 serve to trap the leakage of the absorbing liquid from the scrubbers 17, 18, 19, and 20 and the moisture from waterdrops induced by pressure difference, respectively. The traps 33, 34, 35, and 36 are located at levels lower than those of the corresponding scrubbers 17, 18, 19, and 20. Inlets of the traps 33, 34, 35, and 36 are connected to the ports of the corresponding scrubbers 17, 18, 19, and 20, respectively. Outlets of the traps 33, 34, 35, and 36 are connected to the ports of the corresponding MFCs 29, 30, 31, and 32, respectively.

The MFCs 29, 30, 31, and 32 serve to adjust the flowing or sucking rate of the pumps 9, 10, 11, and 12 or to keep the sucking rate at a specific value. For example, the MFCs 29, 30, 31, and 32 keeps the flowing rate of the pumps 9, 10, 11, and 12 at 0.5 l/min. The MFCs 29, 30, 31, and 32 are connected to the suction ports of the corresponding pumps 9, 10, 11, and 12.

The pumps 9, 10, 11, and 12 are used to suck the air at the sampling points P1 to P10 in the clean room to the diffusion scrubbers 17, 18, 19, and 20 through the air paths 17a, 18a, 19a, and 20a, respectively. The exhaust ports of the pumps 9, 10, 11, and 12 are connected to the traps 37, 38, 39, and 40, respectively. The traps 37, 38, 39, and 40 serve to trap the waterdrops induced by pressure difference or the like. The traps 37, 38, 39, and 40 are located at levels lower than those of the corresponding pumps 9, 10, 11, and 12.

A pre-treatment pump 13 serves to suck the absorbing liquid stored in a container (not shown) through a degasser 41 and sends it to the valve 1. The valve 1 serves to supply alternately the absorbing liquid thus sucked to one of the diffusion scrubbers 17 and 18. Also, the valve 1 serves to discharge the absorbing liquid having passed through the diffusion scrubber 17 or 18 to the outside.

A pre-treatment pump 16 serves to suck the absorbing liquid stored in a container (not shown) through a degasser 44 and sends it to the valve 5. The valve 5 serves to supply alternately the absorbing liquid thus sucked to one of the diffusion scrubbers 19 and 20. Also, the valve 5 serves to discharge the absorbing liquid having passed through the diffusion scrubber 19 or 20 to the outside.

As described above, each of the diffusion scrubbers 17, 18, 19, and 20 causes the trace substances contained in the air to be absorbed into the absorbing liquid flowing through the inside of the corresponding scrubber 17, 18, 19, or 20. This configuration is already known by the Japanese Non-Examined Patent Publication No. 8-54380 and soon.

An absorbing-liquid-circulating pump 14 serves to suck the absorbing liquid stored in a container (not shown) through a degasser 42 and a valve 3. Also, the pump 14 serves to circulate the absorbing liquid thus sucked through a circulating path by way of the pump 14, a valve 4, the concentration column 26, the vale 2, the valve 1, the diffusion scrubber 17 or 18, the valve 1, the valve 2, a trap 50, and the valve 3. The degasser 42 serves to remove foams existing in the absorbing liquid, Similarly, an absorbing-liquid-circulating pump 15 serves to suck the absorbing liquid stored in a container (not shown) through a degasser 43 and a valve 7. Also, the pump 15 serves to circulate the absorbing liquid thus sucked through a circulating path by way of the pump 15, a valve 8, the concentration column 27, the vale 6, the valve 5, the diffusion scrubber 19 or 20, the valve 5, the valve 6, a trap 51, and the valve 7. The degasser 43 serves to remove foams existing in the absorbing liquid.

The valve 4 serves to switch the path to the concentration column 26, thereby supplying alternately one of the absorbing and eluting liquids to the column 26. The valve 8 serves to switch the path to the concentration column 27, thereby supplying alternately one of the absorbing and eluting liquids to the column 27.

The valve 2 is used to discharge the absorbing liquid to the outside during the rinsing operation, in which the residue existing in the concentration column 26 is removed through the valve 2. The valve 6 is used to discharge the absorbing liquid to the outside during the rinsing operation, in which the residue existing in the concentration column 27 is removed through the valve 6.

The valve 3 selects one of the two paths to the circulating pump 14, thereby enabling the pump 14 to suck the absorbing liquid stored in the container through the degasser 42 or that circulating in the circulating path through the trap 50. The valve 7 selects one of the two paths to the circulating pump 15, thereby enabling the pump 15 to suck the absorbing liquid stored in the container through the degasser 43 or that circulating in the circulating path through the trap 51.

As the absorbing liquid, here, ultrapure water with very high purity is used.

The concentration columns 26 and 27 serve to concentrate the cations contained in the absorbing liquid and to bring the concentrated cations to the separation column 28 by using the eluting liquid. The columns 26 and 27 can be connected in series through the two valves 4 and 8.

As the concentration columns 26 and 27, for example, concentration columns termed "TCC-LP1" and produced by Dionex Inc. may be used.

An eluting-liquid-supplying pump 25 serves to suck an eluting liquid stored in a container (not shown) through a degasser 45 and to supply it to the separation column 28 of the analyzer 300 through the valves 4 and 8 and the concentration column 26 or 27. The eluting liquid thus supplied to the separation column 28 is further supplied to the suppressor 60 and the electrical conductivity meter 61 of the analyzer 300 and then, it is discharged to the outside.

(Analyzer)

The separation column 28 separates the desired cation (i.e., ammonia ions) and the other cations from the eluting liquid thus supplied by the pump 25. The suppressor 60 suppresses the electrical conductivity of the background of the eluting liquid. The electrical conductivity meter 61 measures the electrical conductivity of the eluting liquid containing the cations separated by the column 28.

As the eluting liquid, here, a solution of methanesulfonic acid with a concentration of 20 mMol is used.

(Controller)

Although not shown, the controller 400 is comprised of a personal computer, a digital interface, an analog-to-digital (A/D) converter, a patrol light, leakage sensors of water, and pressure sensors. The computer is equipped with a specific control soft ware for the apparatus. The digital interface is used for electrically connecting the computer with the 10-way valves 21 to 24, the valves 1 to 8, the air-sucking pumps 9 to 12, the pre-treatment pumps 13 and 16, the absorbing-liquid-circulating pumps 14 and 15, and the eluting-liquid-sucking pump 25. The A/D converter converts the analog output signals of the electrical conductivity meter 61 to digital signals. The digital signals thus obtained are supplied to the computer through the digital interface. The patrol light displays the state or concentration of the trace substances in the clean room. The leakage sensors are used for sensing the water leakage from the concentration columns 200a and 200b and analyzer 300. The pressure sensors are used for sensing the pressure of the driving fluid for the valves 1 to 8.

The concrete configuration of the controller 400 is disclosed, for example, in the Japanese Non-Examined Patent Publication No. 8-54380.

(Operation Flow)

Figure 9:
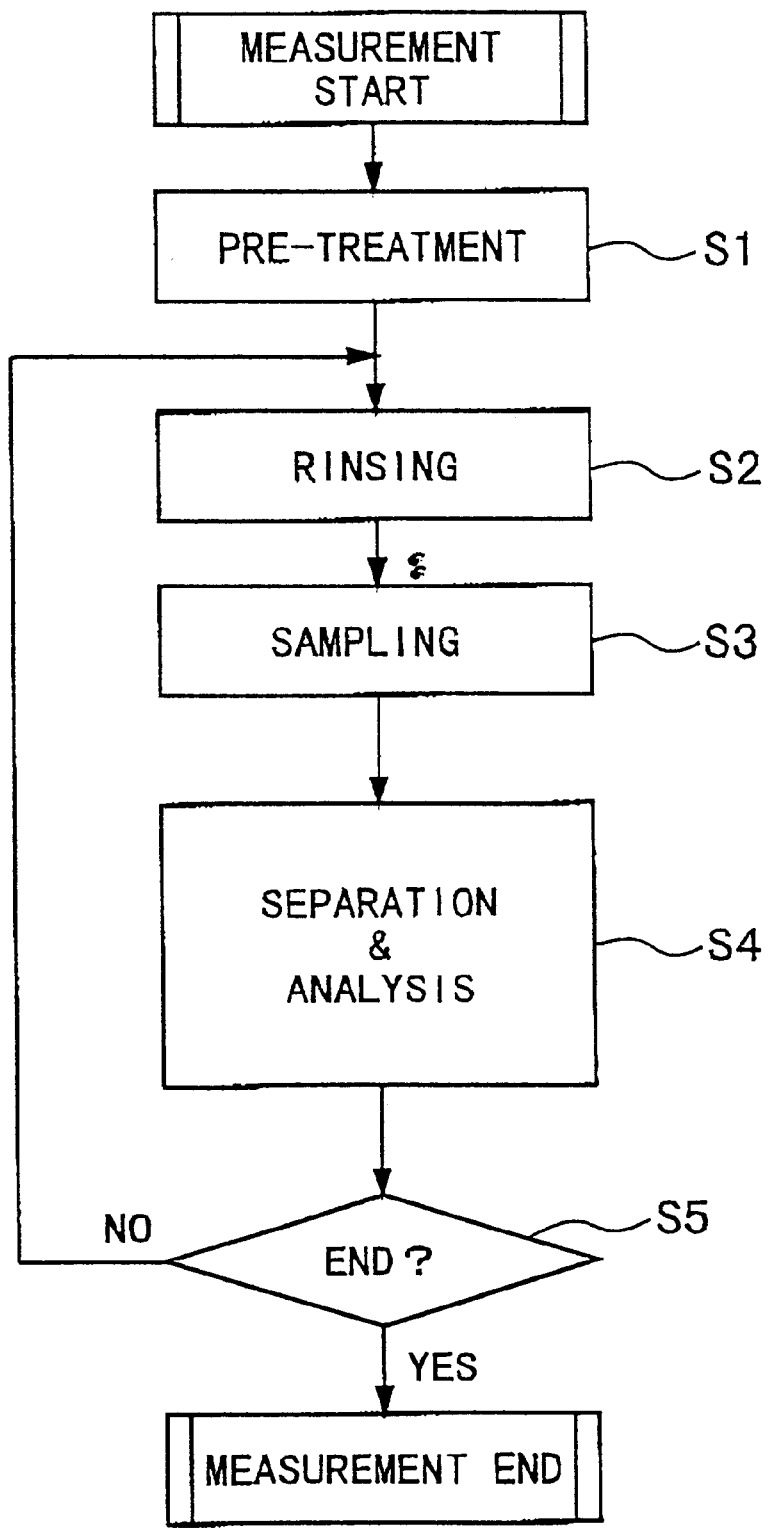
FIG. 9 is a flowchart showing the automatically analyzing steps of the apparatus according to the first embodiment of FIG. 8

FIG. 9 shows the flowchart showing the operation flow of the apparatus according to the first embodiment.

In the step S1, the "pre-treatment operation" is carried out, in which the absorbing liquid (i.e., ultrapure water) is supplied to the diffusion scrubbers 17, 18, 19, and 20 to clean their inside and the relating flow paths. Thus, the remaining trace substances in a prior measurement step are removed. The absorbing liquid thus supplied is then discharge to the outside In the step S2, the "rinsing operation" is carried out, in which the absorbing liquid (i.e., ultrapure water) is supplied to the concentration columns 26 and 27 to clean the inside of the columns 26 and 27 and the relating flow paths. Thus, the remaining eluting liquid in a prior measurement step is removed. The absorbing liquid thus supplied is then discharged to the outside.

In the step S3, the "sampling operation" is carried out, in which the sampled air and the absorbing liquid (i.e. , ultrapure water) are supplied to the diffusion scrubbers 17, 18, 19, and 20. The trace substances contained in the sampled air are absorbed into the absorbing liquid in the scrubbers 17, 18, 19, and 20. The absorbing liquid having the absorbed trace substances is supplied to the concentration column 26 or 27, thereby concentrating and holding the substances in the column 26 or 27. The absorbing liquid from which the substances have been extracted is returned to the scrubbers 17, 18, 19, and 20.

In the step S4, the "separation/analysis operation" is carried out, in which the trace substances are separated from the eluting liquid and then, they are quantitatively analyzed in the ion chromatograph 70.

In the step 5, it is judged whether the analysis process is completed or not. If it has been completed, the flow is stopped. If it has not been completed, the flow is returned to the step S2 and then, the steps S2 to S4 are performed again. Table 1 shows the switching/assignment operation of the four 10-way switch valves 21, 22, 23, and 24.

TABLE 1

| | MEASUREMENT TIMES | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| SAMPLING POINT OF VALVE 21 | P1 | P5 | P9 | P3 | P7 | P1 | P5 | P8 | P1 | P5 | P9 | P3 |
| SAMPLING POINT OF VALVE 22 | P2 | P6 | P10 | P4 | P8 | P2 | P6 | P9 | P2 | P6 | P10 | P4 |
| SAMPLING POINT OF VALVE 23 | P3 | P7 | P1 | P5 | P9 | P3 | P7 | P10 | P3 | P7 | P1 | P5 |
| SAMPLING POINT OF VALVE 24 | P4 | P8 | P2 | P6 | P10 | P4 | P4 | P4 | P4 | P8 | P2 | P6 |

↑ X  ↑ Y

As seen from Table 1, the valve 21 connects the sampling point P1 with the diffusion scrubber 17 at the first measurement. At this time, the valves 22, 23, and 24 connect the sampling points P2, P3, and P4 with the diffusion scrubbers 18, 19, and 20, respectively .

At the second measurement, the valves 21, 22, 23, and 24 connect the sampling points P5, P6, P7, and P8 with the diffusion scrubbers 17, 18, 19, and 20, respectively. The assignment of the sampling points P1 to P10 is carried out in the predetermined sequence or manner shown in Table 1 at the third measurement or later.

The timing of the switching operation of the valves 21 to 24 is as follows.

The sampling point of each of the valves 21, to 24 is transferred to a next one at the time to start the separation/analysis operation in a present measurement step. Then, the pre-treatment operation is carried out for the next one of the sampling points P1 to P10.

The pre-treatment operation is started after the sampling operation is completed. The duration of the pre-treatment operation is controlled by the controller 400 to be as long as possible in order to avoid the effect of the difference in amount and sort of the trace substances at the sampling points P1 to P10. Also, the valves 21 to 24 are controlled in such a way that the air in the clean room is not sampled at the same sampling points in the same measurement step. This makes it possible to use commonly the ten sampling tubes T1 to T10 for the four valves 21 to 24.

Here, as shown in Table 1, it is supposed that the sample air sampled at the point P4 contains a high-concentration desired substance (i.e., ammonia), in other words, the measured concentration of the ammonia exceeds the specific warning limit necessitating a specific caution or warning, in the sixth measurement step. This is shown by a character X at the bottom of Table 1. In this case, under the control of the controller 400, the diffusion scrubber 20 connected to the 10-way valve 24 is used to continue the sampling and measurement operations at the same sampling point P4 while the remaining three diffusion scrubbers 17, 18, and 19 connected to the 10-way valves 21, 22, and 23 are used to perform the above-described sampling and measurement operations at the nine sampling points P1 to P3 and P5 to P10 other than P4. Thus, the sampling point P4 in question is continuously monitored and at the same time, the remaining nine sampling points P1 to P3 and P5 to P10 are alternately monitored by using the three diffusion scrubbers 17, 18, and 19 in the specific sequence.

The continuous or concentrated monitoring for the point P4 is maintained until the ammonia concentration at the point P4 is equal to or less than the specific warning limit. In Table 1, it is supposed that the ammonia concentration at the point P4 is equal to or less than the specific warning limit in the ninth measurement step. This is shown by a character Y at the bottom of Table 1. In the tenth measurement step or later, the popular assignment of the ten sampling points P1 to P10 is carried out in the predetermined sequence.

Figure 10:
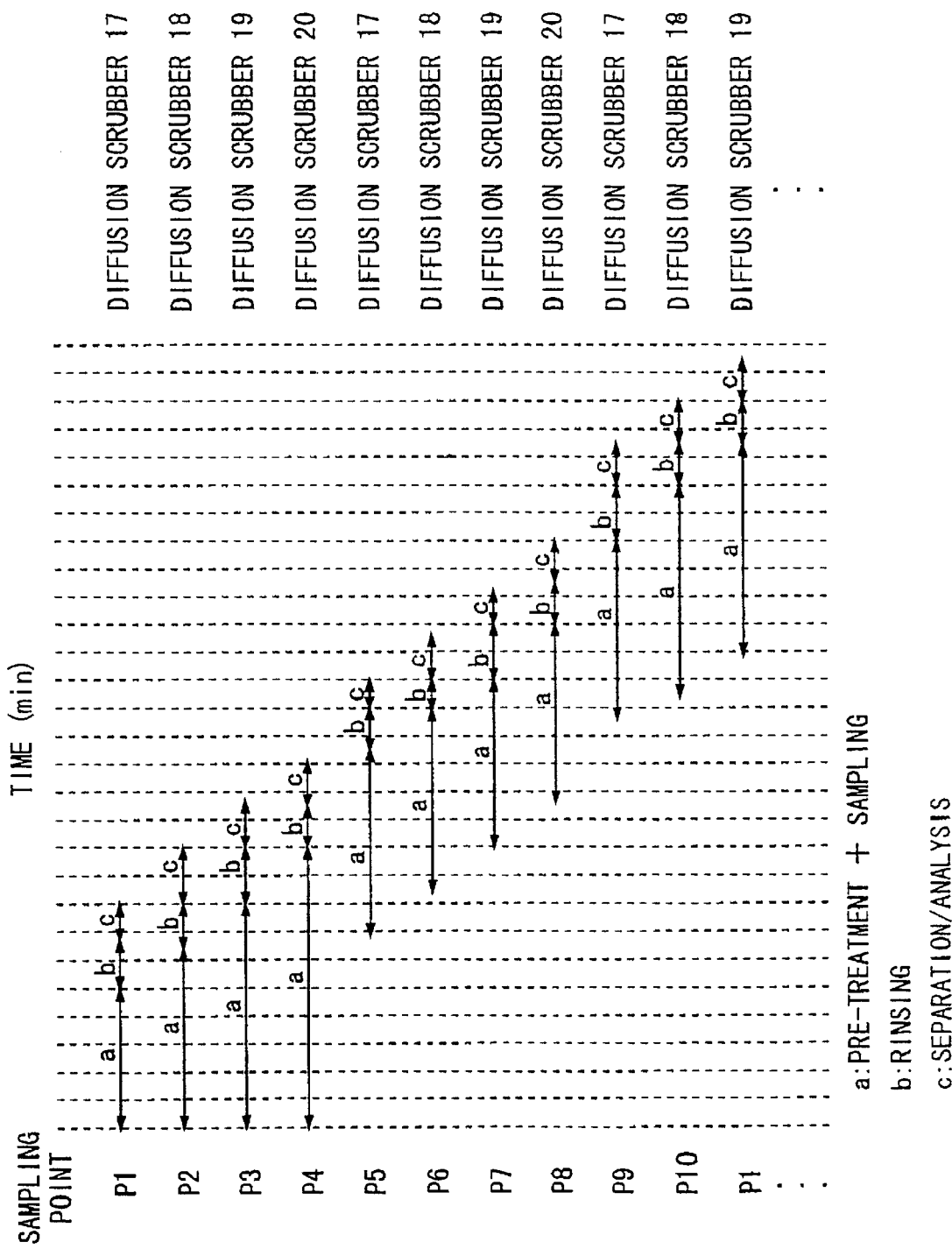
FIG. 10 is a diagram showing the schedule of the individual operations for the ten sampling points in the apparatus according to the first embodiment of FIG. 8.

The assignment of the diffusion scrubbers 17, 18, 19, and 20 to the sampling points P1 to P10 is scheduled according to the sequence shown in Table 1. An example of the schedule is shown in FIG. 10. In FIG. 10, the reference character a denotes the total duration of the pre-treatment and sampling operations, the reference character b denotes the duration of the rinsing operation, and the reference character c denotes the duration of the separation/analysis operation.

Next, the operation of the diffusion scrubbers 17, 18, 19, and 20 and the flow of the sampled air and the absorbing and eluting liquids are explained in more detail below.

Each of the diffusion scrubbers 17, 18, 19, and 20 is repeatedly subjected to one of the pre-treatment, rinsing, sampling, and separation/analysis operations according to the schedule shown in FIG. 10. For example, the duration of each operation is set as 25 minutes for the pre-treatment operation, 0.5 minute for the rinsing operation, 7.5 minutes for the sampling operation, and 8 minutes for the separation/analysis operation.

The flow path comprising the diffusion scrubber 17 and the concentration column 26 constitute a "first flow line".

In the pre-treatment operation of the first flow line, the absorbing liquid flows as follows. Specifically, the absorbing liquid is sucked by the pre-treatment pump 13 from the unillustrated container and then, is supplied to the inside of the diffusion scrubber 17 by way of the valve 1 and the liquid path 17b. The absorbing liquid in the scrubber 17 is moved to the valve 1 again, thereby being discharged to the outside through the valve 1. At this time, the path for the eluting liquid comprising the concentration column 26 is used for the operation for the diffusion scrubber 18.

In the rinsing operation of the first flow line, the absorbing liquid is sucked by the circulating pump 14 from the unillustrated container through the valve 3 and then, is supplied to the inside of the concentration column 26 by way of the valve 4. The absorbing liquid thus supplied removes the residue in the column 26. The absorbing liquid containing the residue is discharged to the outside through the valve 2.

In the sampling operation of the first flow line, the absorbing liquid, which is sucked by the circulating pump 14 from the unillustrated container, is circulated along the path by way of the valve 4, the concentration column 26, the valve 4, the valve 2, the valve 1, the diffusion scrubber 17, the valve 1, the valve 2, the trap 50, the valve 3, and the pump 14. During this circulation, the absorbing liquid absorbs the trace substances (i.e., the water-soluble cations) contained in the sampled air and at the same time, the absorbed substances are concentrated by the concentration column 26 and held therein.

The eluting liquid, which is sucked by the pump 25 from the unillustrated container through the degasser 45, is supplied to the separation column 28 through the valves 4 and 8. The eluting liquid does not pass through the concentration columns 26 and 27. The eluting liquid supplied to the separation column 28 is discharged to the outside through the suppressor 60 and the electrical conductivity meter 61.

The paths of the valve 8 are determined according to the operations of the diffusion scrubbers 19 and 20. Specifically, the valve 8 allows the eluting liquid to pass through the column 27 for sampling or to bypass the column 27 for separation and analysis.

In the separation/analysis operation of the first flow line, the absorbing liquid, which is sucked by the circulating pump 14 from the unillustrated container, is moved along the path by way of the valve 4, the valve 2, the valve 1, the diffusion scrubber 17, the valve 1, the valve 2, the trap 50, and the valve 3, thereby being discharged to the outside from the valve 3. At this time, the absorbing liquid does not pass through the concentration column 26. On the other hand, the eluting liquid, which is sucked by the pump 25 from the unillustrated container through the degasser 45, is moved through the valve 4, the concentration column 26, the valve 4, the valve 8, the separation column 28, the suppressor 60, and the electrical conductivity meter 61, thereby being discharged to the outside. The eluting liquid does not pass through the concentration column 27.

The eluting liquid passing through the concentration column 26 elutes the desired substances (i.e., the water-soluble cations) concentrated and held in the column 26. The separation column 28 separates the desired substances or water-soluble cations thus eluted from the eluting liquid. The suppresser 60 suppresses or lowers the electrical conductivity of the background of the eluting liquid. The electrical conductivity meter 61 measures successively the electrical conductivity of the desired substances thus separated (i.e., water-soluble cations) thereby producing measured values of the electrical conductivity of the individual substances or cations at different, successive times. The meter 61 outputs the analog signals corresponding to the measured values of the electrical conductivity to the personal computer in the controller 400.

The flow path comprising the diffusion scrubber 18 and the concentration column 26 constitute a "second flow line".

The pre-treatment, rinsing, sampling, and separation/analysis operations of the second flow line are the same as those of the above-explained first flow line, except that the paths or ways in the valve 1 are opposite to those for the first flow line in the pre-treatment, rinsing, and sampling operations, thereby moving the absorbing liquid through the diffusion column 18.

The flow path comprising the diffusion scrubber 19 and the concentration column 27 constitute a "third flow line".

In the pre-treatment operation of the third flow line, the absorbing liquid is sucked by the pre-treatment pump 16 from the unillustrated container and then, is supplied to the inside of the diffusion scrubber 19 by way of the valve 5 and the liquid path 20b. The absorbing liquid in the scrubber 19 is moved to the valve 5 again, thereby being discharged to the outside through the valve 5. At this time, the flow paths for the eluting liquid comprising the concentration column 27 are used for the operation for the diffusion scrubber 20.

In the rinsing operation of the third flow line, the absorbing liquid is sucked by the circulating pump 15 from the unillustrated container through the valve 8 and then, is supplied to the inside of the concentration column 27 by way of the valve 8. The absorbing liquid thus supplied removes the residue in the column 27. The absorbing liquid containing the residue is discharged to the outside through the valve 6.

In the sampling operation of the third flow line, the absorbing liquid, which is sucked by the circulating pump 15 from the unillustrated container, is circulated along the path by way of the valve 8, the concentration column 27, the valve 8, the valve 6, the valve 5, the diffusion scrubber 19, the valve 5, the valve 6, the trap 51, the valve 7, and the pump 15. During this circulation, the absorbing liquid absorbs the trace substances (i.e., the water-soluble cations) contained in the sampled air and at the same time, the absorbed substances are concentrated by the concentration column 27 and held therein.

The eluting liquid, which is sucked by the pump 25 from the unillustrated container through the degasser 45, is supplied to the separation column 28 through the valves 4 and 8. The eluting liquid does not pass through the concentration columns 26 and 27. The eluting liquid supplied to the separation column 28 is discharged to the outside through the suppressor 60 and the electrical conductivity meter 61.

The paths of the valve 4 are determined according to the operations of the diffusion scrubbers 17 and 18. Specifically, the valve 4 allows the eluting liquid to pass through the column 26 for sampling or to bypass the column 26 for separation and analysis.

In the separation/analysis operation of the third flow line, the absorbing liquid, which is sucked by the circulating pump 15 from the unillustrated container, is moved along the path by way of the valve 8, the valve 6, the valve 5, the diffusion scrubber 19, the valve 5, the valve 6, the trap 51, and the valve 7, thereby being discharged to the outside from the valve 7. At this time, the absorbing liquid does not pass through the concentration column 27. On the other hand, the eluting liquid; which is sucked by the pump 25 from the unillustrated container through the degasser 45, is moved through the valve 4, the concentration column 27, the valve 4, the valve 8, the separation column 28, the suppressor 60, and the electrical conductivity meter 61, thereby being discharged to the outside. The eluting liquid does not pass through the concentration column 26.

The eluting liquid passing through the concentration column 27 elutes the desired substances (i.e., the water-soluble cations) concentrated and held in the concentration column 27. The separation column 28 separates the desired substances or water-soluble cations thus eluted. The operation of the suppressor 60 and the electrical conductivity meter 61 are the same as those described above for the first flow line.

The flow path comprising the diffusion scrubber 18 and the concentration column 26 constitute a "fourth flow line".

The pre-treatment, rinsing, sampling, and separation/analysis operations of the fourth flow line are the same as those of the above-explained third flow line, except that the paths or ways in the valve 5 are opposite to those for the third flow line in the pre-treatment, rinsing, and sampling operations, thereby moving the absorbing liquid through the diffusion column 20.

(Trap)

Next, the operation of the traps 50 and 51, which are provided respectively at the suction sides of the pumps 14 and 15 through the valves 3 and 7, are explained below.

Figure 11:
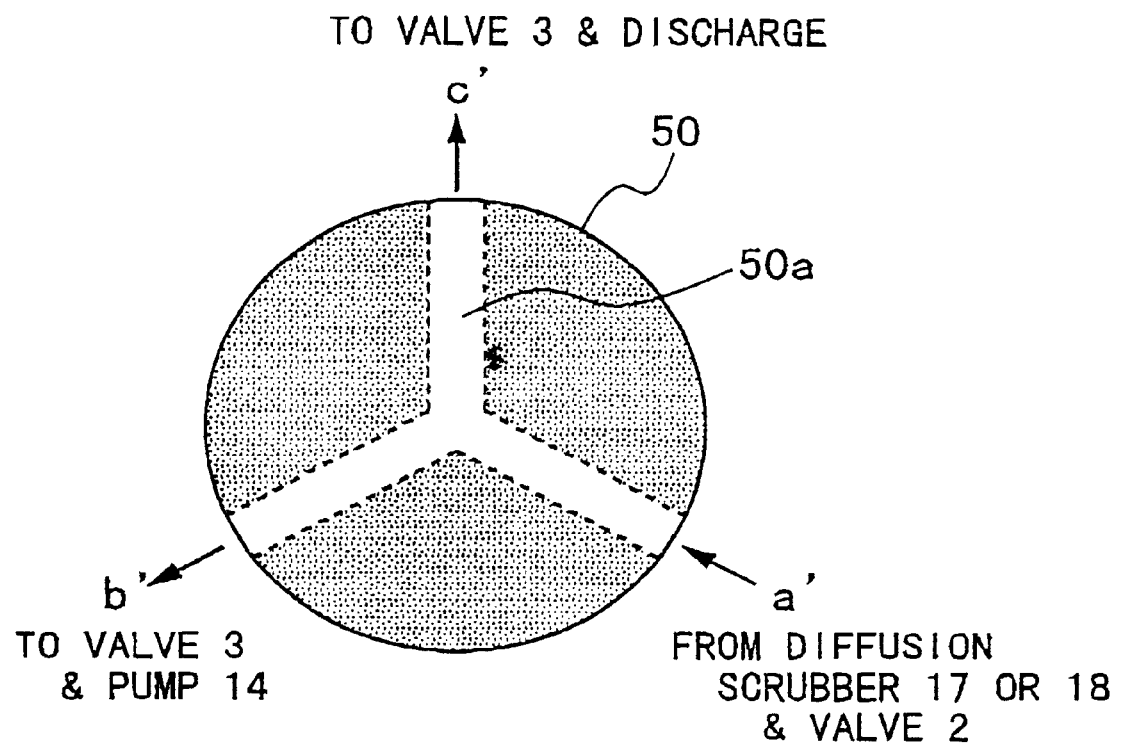
FIG. 11 is a schematic view showing the configuration of a trap used in the apparatus according to the first embodiment of FIG. 8.

The traps 50 and 51 serve to remove the air foams contained in the absorbing liquid, thereby preventing malfunction of the pumps 14 and 15 due to the foams. FIG. 11 shows schematically the structure of the trap 50.

In the sampling operation, the valve 3 have the ways shown by broken lines in FIG. 8. Therefore, the port c' of the trap 50 in FIG. 11 is closed, resulting in the way connecting the port a' with the port b'. Thus, the absorbing liquid supplied from the diffusion scrubber 17 or 18 through the valve 2 flows through the trap 50 at the ports a' and b'. Since the trap 50 is fixed in such a way that the port c' is located upward, only the foams contained in the absorbing liquid flowing through the trap 50 are trapped in its reservoir 50a and are not moved to the valve 3. This means that the foams are effectively removed from the absorbing liquid by the trap 50.

The separation/analysis operation begins after the sampling operation is completed. In the separation/analysis operation, the valve 3 have the ways shown by solid lines in FIG. 8. Therefore, the port b' of the trap 50 in FIG. 11 is closed, resulting in the way connecting the port a' with the port c' Thus, not only the absorbing liquid supplied from the diffusion scrubber 17 or 18 but also the trapped foams in the reservoir 50a flow out of the trap 50 through the port c' to be discharged.

Subsequently, when the sampling operation is started again, no foam exists in the reservoir 50a. Therefore, the foams having a same volume as that of the reservoir 50a can be removed.

The same explanation as to the trap 50 is applied to the trap 51.

Figure 5:
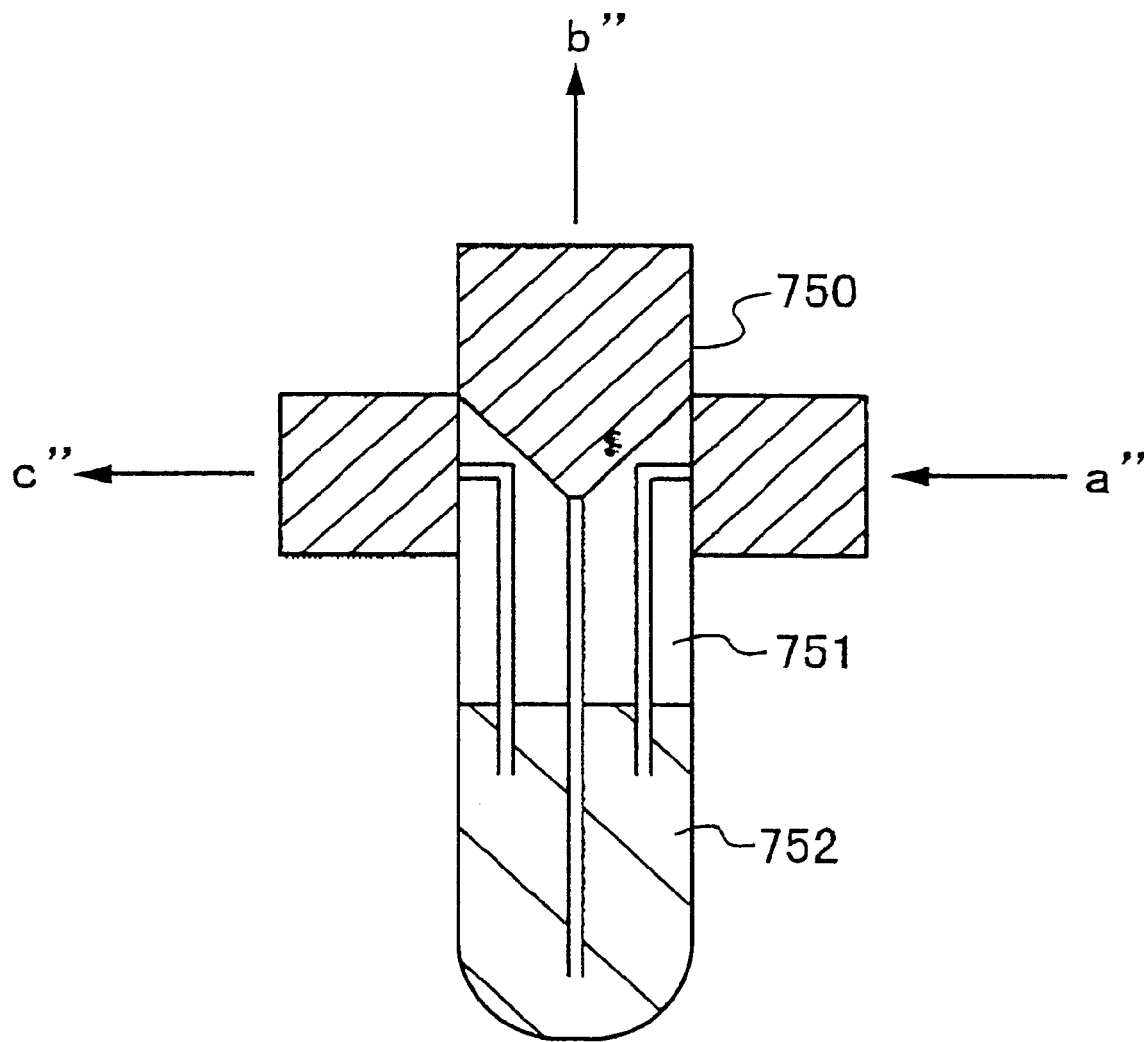
FIG. 5 is a schematic view showing the configuration of a trap used in the prior-art apparatus shown in FIG. 1 or 3.

FIG. 5 shows a prior-art trap 750, which may be used as the trap 50 or 51. The ports a", b", and c" correspond to the ports a', b', and c' of the trap 50, respectively.

In the prior-art trap 750 of FIG. 5, in the sampling operation, the port c" of the trap 750 is closed, resulting in the way connecting the port a" with the port b". Thus, the absorbing liquid supplied from the diffusion scrubber 17 or 18 through the valve 2 flows into the trap 750 through the port a" and flows out of the trap 750 through the port c". Only the foams contained in the absorbing liquid flowing into the trap 750 are trapped in its reservoir 751 and are not moved to the valve 3. The reference numeral 752 is the absorbing liquid stored in the trap 750. The inner space over the store liquid 752 serves as the reservoir 751.

The absorbing liquid 752 stored in the trap 750 contains a part supplied in a prior measurement step or steps and a part of the present measurement step, which is sent out of the trap 750 and sent to the valve 3. Therefore, if any one of the prior measurement steps deals with the sampled air containing a high-concentration substance, the present measurement step is readily affected by the residue of the substance, i.e., the memory effect.

On the other hand, in the trap 50 used in the first embodiment of FIG. 11, even if any one of the prior measurement steps deals with the sampled air containing a high-concentration substance, the present measurement step is scarcely affected by the residue of the substance, i.e., the memory effect. This is due to the fact that the absorbing liquid is not stored in the trap 50 unlike the stored liquid 751 in the prior-art trap 750.

(Controller)

With respect to the samplers 100a, 100b, 100c, and 100d and the concentrators 200a and 200b, the controller 400 controls the switching operation of the 10-way valves 21 to 24, the driving operation of the air-absorbing pumps 9 to 12, and the display or indication of the operating state of the pumps 9 to 12. Also, the controller 400 controls the switching operation of the valves 1 to 8, the driving operation of the pre-treatment pumps 13 and 16, the driving operation of the circulating pumps 14 and 15, the display or indication of the operating state of the pumps 14 to 15.

With respect to the analyzer 300, the controller 400 controls the driving operation of the eluting-liquid pump 25, the display or indication of the operating state of the pump 25, the converting operation of the analog signals (i.e., analog data) from the electrical conductivity meter 61 to the digital signals (i e., digital data), the input operation of the digital signals thus produced into the personal computer, the identification and concentration-calculation operations of the desired gaseous substance (i.e., ammonia) for the digital data about the electrical conductivity of the trace substances (i.e., the water-soluble cations), the display operation of the calculated concentration of the ammonia, the schedule of the pre-treatment, rinsing, sampling, and separation/analysis operations, the monitoring operation of the water-Leakage and pressure sensors, detection of a high-concentration state of ammonia, the turn-on and turn-off operation of the patrol light at the time a high-concentration of ammonia or any one of specific alarm states is detected, and calculation of the total concentration of ammonia accumulated in a specific period of time.

(Scheduling)

The schedule of the pre-treatment, rinsing, sampling, and separation/analysis operations are preferably assigned in the following way.

First, to enable the analyzer 300 to perform its analyzing operation (i.e., the quantitatively analysis of ammonia) continuously or without any waiting time, one of the two concentrators 200a and 200b (i.e., the concentration columns 26 and 27) is controlled to perform the separation/analysis operation and at the same time, the other is controlled to perform the rinsing and sampling operations for a next measurement step. Therefore, when the duration times of the separation/analysis, rinsing, and sampling operations are defined as $t_{sa}$, $t_r$, and $t_s$, respectively, they are determined to satisfy the following relationship (4). This is the "first condition".

$$t_{sa} = t_r + t_s \quad (4)$$

Moreover, the two samplers 100a and 100b corresponding to the concentrator 200a and the two samplers 100c and 100d corresponding to the concentrator 200b need to be controlled not to perform simultaneously the sampling operation and separation/analysis operation. This is the "second condition".

If the schedule and assignment of the duration of the separation/analysis, rinsing, and sampling operations are so defined as to satisfy the above-described first and second conditions, the analyzer 300 is able to continuously perform the separation/analysis operation for the two concentrators 200a and 200b without any waiting time. In this case, the cycle time of the whole measurement sequence can be minimized.

With the apparatus for automatically analyzing a trace substance (i.e., ammonia) according to the first embodiment of FIGS. 6 to 8, since the analyzer 300 is controlled by the controller 400 to receive successively the concentrated substances from the concentrator 200a or 200b, the analyzer 300 performs its analyzing operation with no idle or waiting time. Thus, the cycle time of the analyzing operation for all the sampling points P1 to P10 can be shortened.

Also, the ten sampling tubes T1 to T10, which are respectively connected to the ten sampling points P1 to P10, are commonly connected to the four samplers 100a to 100d. Each of the four samplers 100a to 100d performs its sampling operation of the air in the clean room at different sampling points. Therefore, the number of necessary switch valves can be decreased, i.e., the switching operation of the sampling points P1 to P10 can be realized by only the four switch valves 21 to 24.

Since the traps 50 and 51 having the structure shown in FIG. 11 are used for removing the air foams existing in the absorbing liquid, the so-called memory effect of the remaining trace substances can be further suppressed.

If the sample air sampled at any of the sampling points P1 to P10 contains a high-concentration desired substance (i.e., ammonia), in other words, the measured concentration of the ammonia exceeds the specific warning limit necessitating a specific caution or warning, a specific one of the four samplers 100a to 100d is assigned to continue the sampling and measurement operations at the same sampling point. Thus, even if a high-concentration substance is suddenly generated in the clean room, the generation of the high-concentration substance can be surely detected and monitored.

Since the total concentration of the desired substance (i.e., ammonia) accumulated in a specific period of time can be obtained, the desired substance can be monitored accurately.

There is an additional advantage that any one or ones of the four samplers 100a to 100d can be used for analyzing another trace substance existing in the sampled air. For example, one of the samplers 100a to 100d can be used for analyzing water-soluble amine by the known Denuda method. As a result, two or more substances in the clean room can be analyzed and monitored at different sampling points.

Second Embodiment (Basic Configuration)

Figure 12:
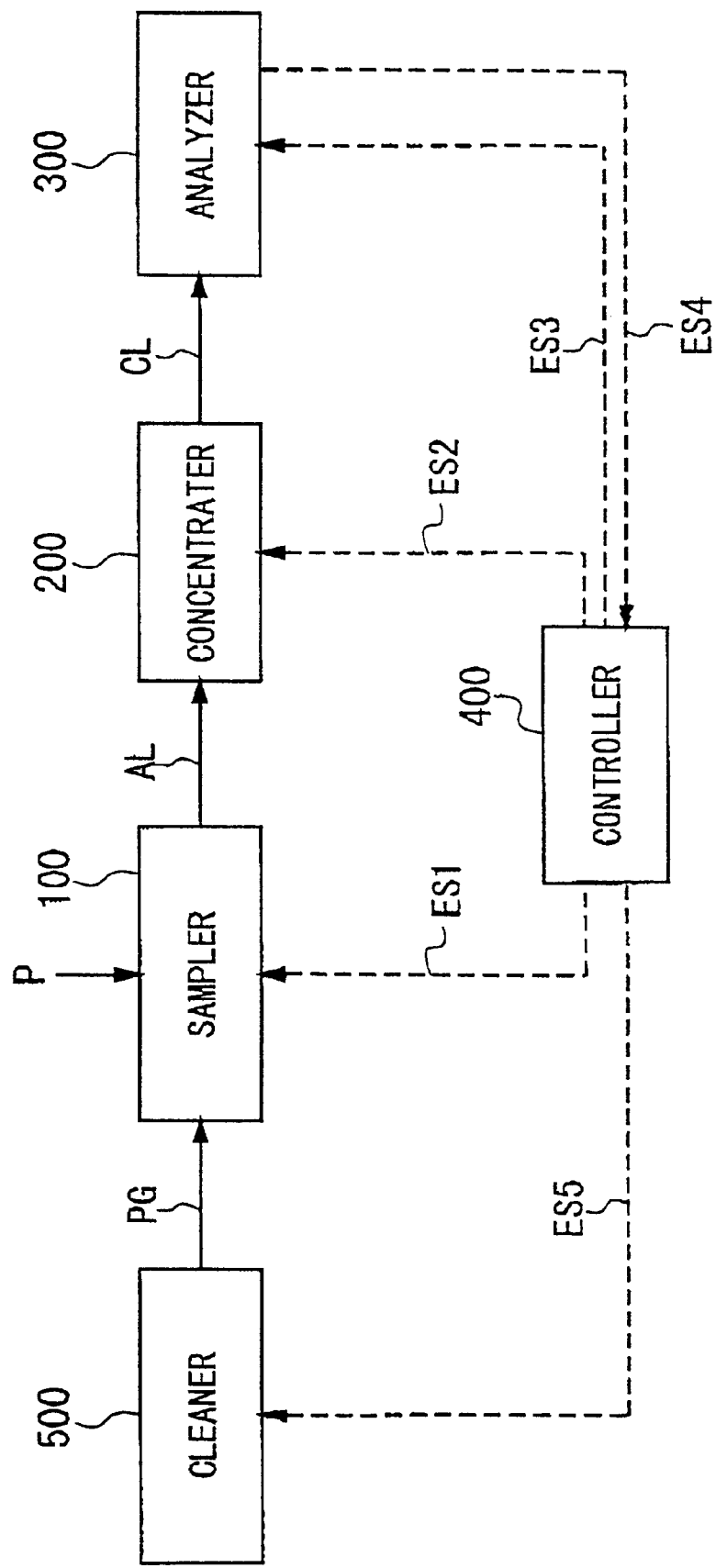
FIG. 12 is a schematic block diagram showing the configuration of an apparatus for automatically analyzing a trace substance according to a second embodiment of the present invention.

An apparatus for automatically analyzing a trace substance according to a second embodiment of the present invention has a basic configuration shown in FIG. 12. Specifically, the apparatus is comprised of a sampler 100, a concentrator 200, an analyzer 300, a controller 400, and a cleaner 500.

The sampler 100, which is connected with a sampling point P in a clean room for semiconductor device fabrication, produces a sample of the air in the clean room at the point P. The sampled air contains trace substances such as ammonia and monoethanolamine existing in the air. The trace substances in the sampled air are then absorbed into an absorbing liquid, thereby producing a sample AL of the trace substances.

The concentrator 200 is connected to the sampler 100. The concentrator 200 receives the sample AL of the trace substances from the sampler 100 and then, concentrates the trace substances absorbed into the absorbing liquid, thereby producing a concentrated sample CL. The concentrated sample CL of the substances is then sent to the analyzer 300.

The analyzer 300 is connected to the concentrator 200. The analyzer 300 receives the concentrated sample CL of the substances and then, analyzes quantitatively the same, thereby producing a time-dependent concentration data of the desired substances. Thus, the time-dependent concentration change of the trace substances existing in the clean room can be known.

The cleaner 500 cleans the sampler 100 to remove the trace substances remained therein in a prior measurement step by supplying a purging gas PG.

The controller 400 controls the sampler 100, the concentrator 200, the analyzer 300, and the cleaner 500, thereby displaying the time-dependent concentration data of the desired substances and store the same in a suitable storage device and calculating the total amount of the accumulated substances in a specific period of time at the sampling point P.

The reference characters ES1, ES2, ES3, and ES5 in FIG. 12 denote control signals for the sampler 100, the concentrator 200, the analyzer 300, and the cleaner 500, respectively. The reference character ES4 in FIG. 12 denotes a data signal of the analyzed substances outputted from the analyzer 300.

(Detailed Configuration)

Figure 13:
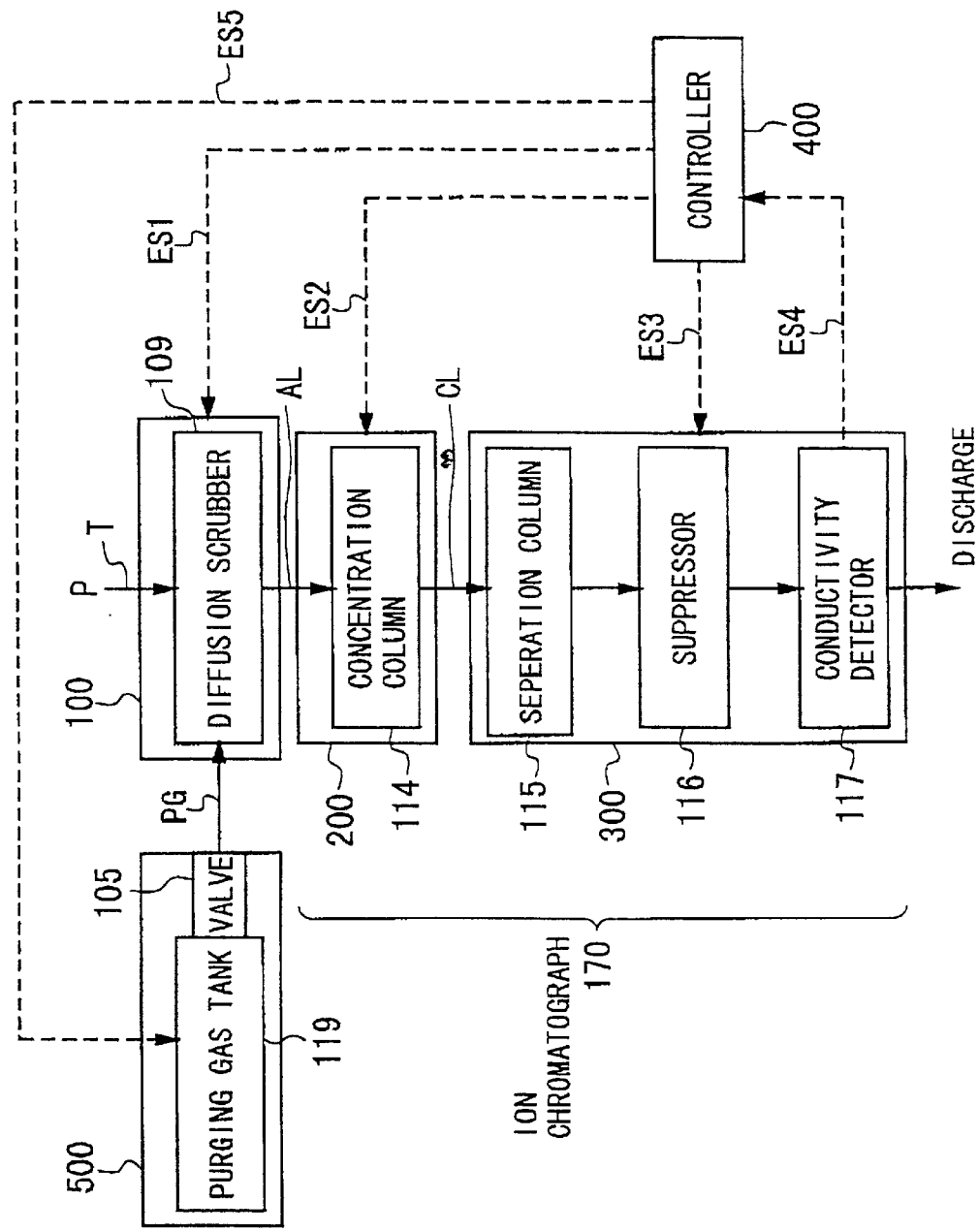
FIG. 13 is a schematic block diagram showing the detailed configuration of the apparatus according to the second embodiment of FIG. 12.

FIG. 13 shows the detailed configuration of the apparatus according to the second embodiment of FIG. 12, in which the structural elements of the sampler 100, the concentrator 200, the analyzer 300, and the cleaner 400 are illustrated.

This apparatus analyzes ammonia and monoethanolamine existing in the clean room as the desired trace substances. Thus, this apparatus may be termed an automatic-analyzing apparatus of ammonia and monoethanolamine.

As shown in FIG. 13, the sampler 100 includes a sampling tube T and a diffusion scrubber 109. The concentrator 200 includes a concentration column 114. The analyzer 300 includes a separation column 115, a suppressor 116, and an electrical conductivity meter 117. The concentration column 114, the separation column 115, the suppressor 116, and the electrical conductivity meter 117 are part of an ion chromatograph 170. The cleaner 500 includes a valve 105 and a purging gas tank 119.

(Concrete Configuration)

Figure 14:
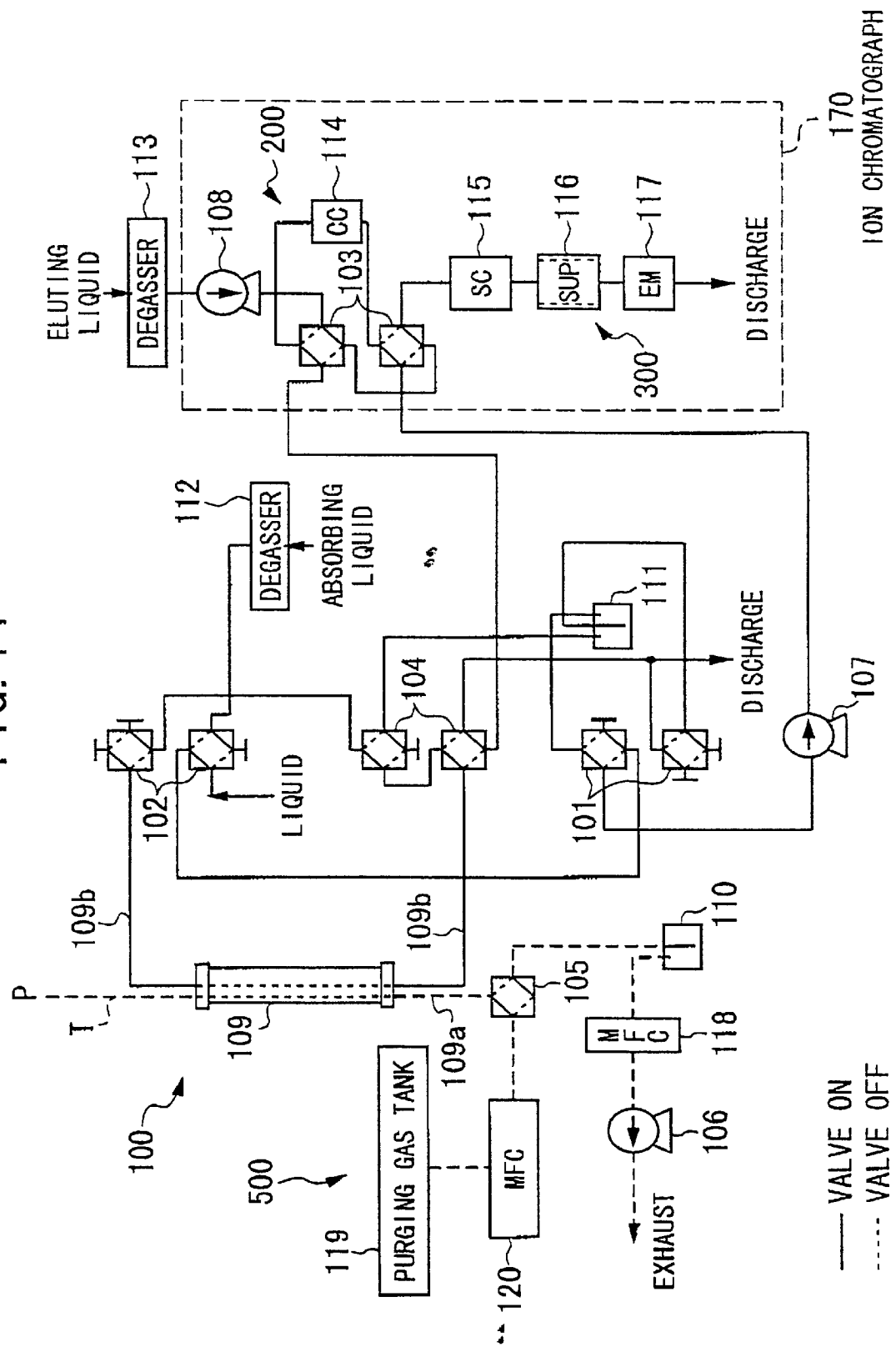
FIG. 14 is a schematic block diagram showing the concrete configuration of the apparatus according to the second embodiment of FIGS. 12 and 13.

FIG. 14 shows a concrete configuration of the apparatus for automatically analyzing trace substance according to the second embodiment of FIGS. 12 and 13, in which connecting tubes and pumps are illustrated in detail.

As shown in FIG. 14, the sampler 100 has the sampling tube T, the diffusion scrubber 109, a trap 110, a MFC 118, and a pump 106 for sucking the air.

The diffusion scrubber 109 has the same configuration as that of the diffusion scrubbers 17, 18, 19, and 20 used in the first embodiment of FIG. 8.

One end of the sampling tube T is located at the sampling point P in the clean room and the other end is connected to the scrubber 109. The air existing in the clean room is sampled at the point P and sent to the scrubber 109 through the tube T due to the sucking operation of the pump 106.

The scrubber 109 has an air path 109a through which the sampled air flows and a liquid path 109b through which an absorbing liquid flows. One end of the air path 109a is connected to the tube T and the other end is connected to a port of the valve 105. The sampled air is sent to the air path 109a through the tube T and the scrubber 109.

The ways in the valve 105 are controlled to connect the air path 109a with the trap 110 in any time except for the cleaning operation, thereby allowing the sampled air to flow through the scrubber 109. In the cleaning operation, the valve 105 is operated to connect the air path 109a with the MFC 120 of the cleaner 500, thereby allowing the purging gas stored in the tank 119 to enter the air path 109a and the inside of the scrubber 109. Thus, the air path 109a and the inside of the scrubber 109 are cleaned.

The trap 110 serves to trap the leakage of the absorbing liquid from the scrubber 109 and the moisture from waterdrops induced by pressure difference. The trap 110 is located at a level lower than that of the scrubber 109.

The MFC 118 serves to adjust the flowing or sucking rate of the pump 106 or to keep the flowing rate at a specific value. For example, the MFC 106 keeps the flowing rate of the pump 106 at 0.5 l/min.

The pump 106 is used to suck the air at the sampling point P in the clean room to the diffusion scrubber 109 through the tube T. The pump 106 is located at the outlet side of the MFC 118.

The concentrator 200 includes a degasser 112, a valve 102, the diffusion scrubber 109, a valve 101, a valve 104, a pump 107 for circulating the absorbing liquid, a trap 111, and the concentration column 114. The trace substances such as ammonia and monoethanolamine absorbed into the absorbing liquid are concentrated and held in the concentrator 114. The trace substances such as ammonia and monoethanolamine are absorbed into the absorbing liquid in the diffusion scrubber 109.

The degasser 112 removes the gas existing in the absorbing liquid. As the absorbing liquid, ultrapure water is used here. The valve 102 switches the ways of the absorbing liquid sucked through the degasser 112. The valve 101 switches the ways of the absorbing liquid sucked by the pump 107, thereby allowing the absorbing liquid to be sucked into the diffusion scrubber 109 or to be circulated. The valve 104 switches the ways of the absorbing liquid sucked by the pump 107, thereby allowing the absorbing liquid to be discharged to the outside in the rinsing operation or to be circulated.

The pump 107 for circulating the absorbing liquid sucks the absorbing liquid containing the desired substances through the degasser 112 and sends it to the valve 103. In the pre-treatment operation, the valves 101, 102, 103, and 104 are all closed and therefore, the absorbing liquid sucked from the unillustrated container flows through the diffusion scrubber 109 and is discharged to the outside by the pump 107.

The trap 111 serves to trap the leakage of the absorbing liquid from the diffusion scrubber 109 and the moisture from waterdrops induced by pressure difference. The trap 111 is located at a level lower than that of the scrubber 109.

The analyzer 300 is comprised of the separation column 115, the suppressor 116, and the electrical conductivity meter 117 of the ion chromatograph 170. The operations of the separation column 115, the suppressor 116, and the electrical conductivity meter 117 are the same as those of the separation column 28, the suppressor 60, and the electrical conductivity meter 61 used in the apparatus according to the first embodiment, respectively.

The desired trace substances concentrated in the concentration column 114 are sent to the analyzer 300 by an eluting liquid and then, separated and quantitatively analyzed in the same way as that shown in the first embodiment. The eluting liquid is sucked by an eluting pump 108 from an unillustrated container through a degasser 113 and is sent to the valve 103. As the eluting liquid, a solution of 20-mMol methanesulfonic acid may be used.

The valve 103 serves also to discharge the absorbing liquid in the rinsing operation to remove the residue in the concentration column 114. In the sampling operation, the valve 103 is opened to connect the diffusion scrubber 109 with the concentration column 114, allowing the trace substances in the absorbing liquid to be accumulated in the column 114.

The concentration column 114 has the same configuration and operation as those of the concentration columns 200a and 200b used in the first embodiment.

Although not shown, the controller 400 is comprised of a personal computer, a digital interface, an A/D converter, a patrol light, leakage sensors of water, and pressure sensors. The computer is equipped with a specific control software for the apparatus. The digital interface is used for connecting the computer with the valves 101 to 105, the air-sucking pumps 106 to 108. The A/D converter converts the analog output signals of the electrical conductivity meter 117 to digital signals and then, supplies the digital data to the computer through the interface. The patrol light displays the state of the substances in the clean room. The leakage sensors are used for sensing the water leakage in the concentrator 200 and the analyzer 300. The pressure sensors are used for sensing the pressure of the driving fluid for the valves 101 to 105.

The cleaner 500 comprises the purging gas tank 119, a MFC 120, and the valve 105, which cleans the inside of the sampling tube T, the diffusion scrubber 109, and the air path 109a. The tank 119 stores the purging gas. As the purging gas, any inert gas such as pure nitrogen gas may be used. The MFC 120 controls the flow rate of the purging gas.

The valve 105 switches the way to the end of the diffusion scrubber 109. In the cleaning operation, the valve 105 is operated to connect the diffusion scrubber 109 with the MFC 120, allowing the purging gas to enter the scrubber 109. In the operations other than the cleaning operation, the valve 105 is operated to connect the diffusion scrubber 109 with the MFC 118, allowing the absorbing gas to be discharged to the outside.

(operation Flow)

Figure 15:
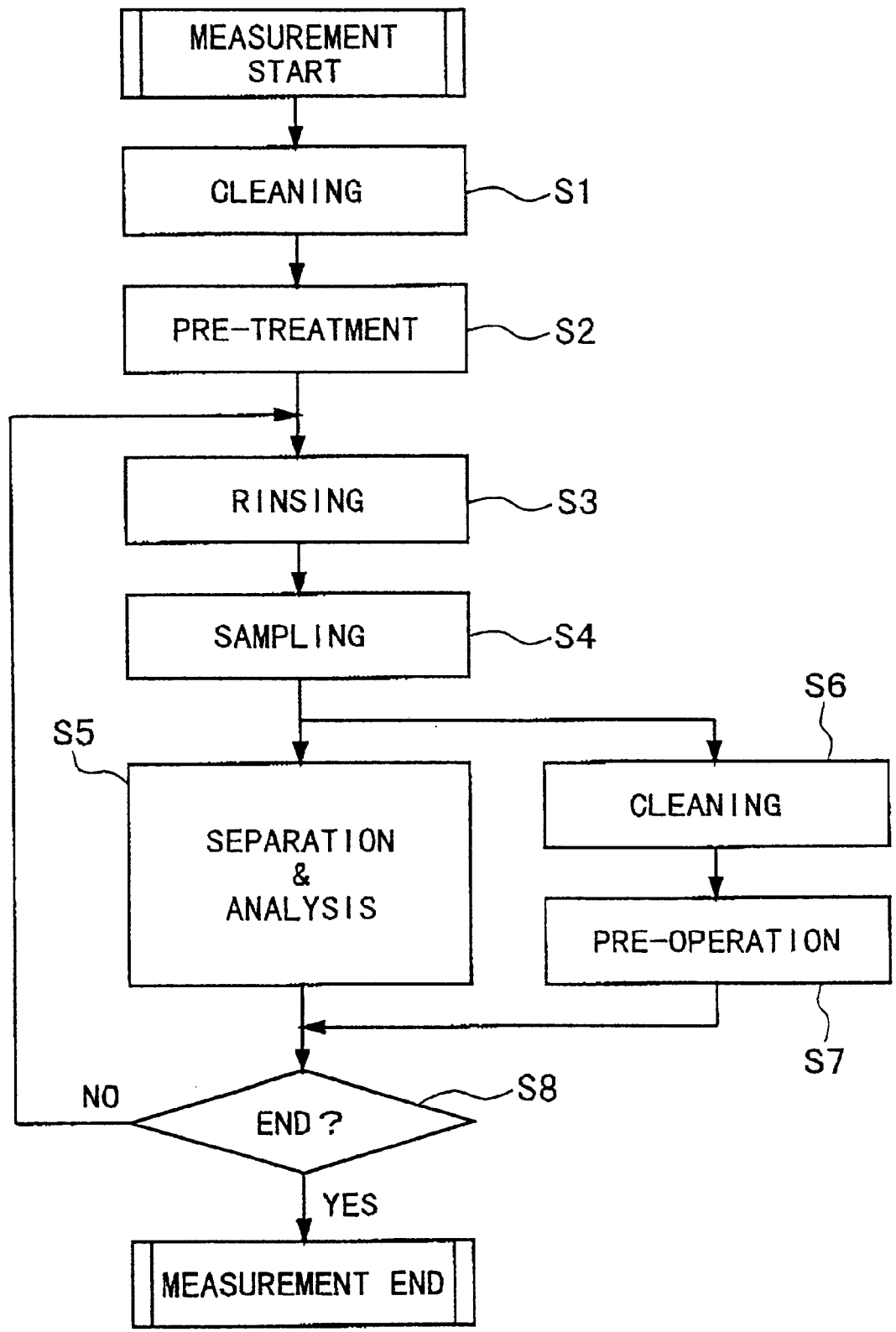
FIG. 15 is a flowchart showing the automatically analyzing steps of the apparatus according to the second embodiment of FIG. 14.

FIG. 15 shows the flowchart showing the operation flow of the apparatus according to the second embodiment.

In the step S1, the "cleaning operation" is carried out, in which the purging gas is supplied to the diffusion scrubber 109, the air path 109a, and the sampling tube T. The purging gas thus supplied is discharged from the end of the tube T at the sampling point T. Thus, the inside of the diffusion scrubber 109, the air path 109a, and the sampling tube T is cleaned.

In the step S2, the "pre-treatment operation" is carried out, in which the absorbing liquid (i.e., ultrapure water) is supplied to the diffusion scrubber 109 to wash its inside and the relating flow paths. Thus, the remaining trace substances are removed or decreased. The absorbing liquid thus supplied is then discharged to the outside.

In the step S3, the "rinsing operation" is carried out, in which the absorbing liquid (i.e., ultrapure water) is supplied to the concentration column 114 to rinse its inside and the relating flow paths. Thus, the remaining eluting liquid is removed. The absorbing liquid thus supplied is then discharged to the outside.

In the step S4, the "sampling operation" is carried out, in which the sampled air and the absorbing liquid (i.e., ultrapure water) are supplied to the diffusion scrubber 119. The trace substances contained in the sampled air are absorbed into the absorbing liquid in the scrubber 109. The absorbing liquid containing the trace substances is then supplied to the concentration column 114, thereby concentrating the substances and held in the column 114. The absorbing liquid from which the substances have been extracted is then returned to the scrubber 109.

In the step S5, the "separation/analysis operation" is carried out, in which the desired substances are separated from the concentrated substances contained in the eluting liquid and then, they are quantitatively analyzed in the ion chromatograph 170.

During the step S5 is carried out, the "cleaning operation" is performed in the step S6 and then, the "pre-treatment operation" is performed in the step S7 for a next measuring step. Thus, the residue of the trace substances in the sampling tube T and the diffusion scrubber 109 generated in a prior measuring step is removed.

In the step S8, it is judged whether the analysis is completed or not. If it has been completed, the flow is stopped. If it has not been completed, the flow is returned to the step S3 and then, the steps S3 to S8 are performed again.

For example, the duration times for the individual operations are defined as follows.

cleaning operation: 1 minute pre-treatment operation: 23 minutes rinsing operation: 0.5 minute sampling operation: 10 minutes separating/analyzing operation: 24 minutes In this case, the total time is 58.5 minutes.

(Paths)

Next, the flow path of the sampled air is explained in more detail below.

In the cleaning operation, the air-sucking pump 106 is stopped and the valve 105 is operated to connect the diffusion scrubber 109 with the purge gas tank 119. Then, the purge gas in the tank 119 is supplied to the inside of the scrubber 109 through the air path 109a at the specific flow rate and then, is discharged to the outside through the tube T.

In the pre-treatment, rinsing, and sampling operations, the valve 105 is closed to connect the diffusion scrubber 109 with the trap 110 while the air-sucking pump 106 is driven to perform its sucking operation. Thus, the air in the clean room is collected or introduced into the scrubber 109.

The flow path of the absorbing liquid is as follows.

In the cleaning and pre-treatment operations, the absorbing liquid is sucked from the container by the pump 107 and is discharged to the outside through the flow path 109b, the diffusion scrubber 109, and the trap 111.

In the rinsing operation, the absorbing liquid is sucked from the container by the pump 107 and is discharged to the outside through the valve 103, the concentration column 114, and the valve 104.

In the sampling operation, the absorbing liquid is sucked from the container by the pump 107 and is circulated through the circulating path comprising the valve 103, the concentration column 114, the valve 103, the valve 104, the diffusion scrubber 109, the valve 102, the valve 104, the trap 111, the valve 101, and the pump 107. Thus, the trace substances contained in the sampled air is absorbed into the absorbing liquid in the diffusion scrubber 109 and then, the absorbed substances into the absorbing liquid are concentrated and held in the concentration column 114.

In the separation/analysis operation, the absorbing liquid is sucked from the container by the pump 107 and is discharged to the outside through the path comprising the valve 101, the valve 101, the valve 103, the valve 104, the diffusion scrubber 109, the valve 102, the valve 104, the trap 111, and the valve 101. The absorbing liquid does not pass through the concentration column 114 in this operation.

Next, the flow path of the eluting liquid is explained below.

In the sampling operation, the eluting liquid is sucked from the container by the pump 108 through the degasser 113 and is discharged to the outside through the valve 103, the separation column 115, the suppressor 116, and the electrical conductivity meter 117. The eluting liquid does not pass through the concentration column 114 in this operation.

In the separation/analysis operation, the eluting liquid is sucked from the container by the pump 108 through the degasser 113 and is discharged to the outside through the valve 103, the concentration column 114, the valve 103, the separation column 115, the suppressor 116, and the electrical conductivity meter 117. In the concentration column 114, the eluting liquid elutes the trace substances concentrated and held in the colamn 114. Thus, the trace substances are included in the eluting liquid.

The separation column 115 separates the desired trace substances in the eluting liquid. The electrical conductivity meter 117 measures the electrical conductivity of the individual substances or cations thus separated, outputting the analog signals corresponding to the values of the electrical conductivity to the computer.

(Controller)

The controller 400 controls the driving operation of the valves and pumps and the display or indication of their operating state in the sampler 100, the concentrator 200, the analyzer 300, and the cleaner 500, and the necessary data processing operation.

The controller 400 further controls the converting operation of the analog signals (i.e., analog data) from the electrical conductivity meter 61 to digital signals (i.e., digital data), the input operation of the digital signals thus produced into the personal computer, the identification and concentration-calculation operations of the desired gaseous substances (i.e., ammonia and monoethanolamine) from the digital data about the electrical conductivity of the trace substances (i.e., the water-soluble cations), the display operation of the calculated concentration of the substances, the scheduling operation of the cleaning, pre-treatment, rinsing, sampling, and separation/analysis operations, the monitoring operation of the water-leakage and pressure sensors, detection of a high-concentration state of the substances (i.e., ammonia and monoethanolamine), the turn-on and turn-off operation of the patrol light at the time a high-concentration of ammonia and/or monoethanolamine or any one of specific alarm states is detected, and calculation of the total concentration of ammonia and monoethanolamine accumulated in a specific period of time. (Scheduling)

To minimize the cycle time of the measuring sequence, the duration times of the separation/analysis, cleaning, and pre-treatment operations are determined to satisfy the following equation (5).

$$t_{sa} = t_c + t_{pt} \tag{5}$$

In the equation (5), $t_{sa}$, $t_c$, and $t_{pt}$ are the duration times of the separation/analysis, cleaning, and pre-treatment operations, respectively.

Figure 16:
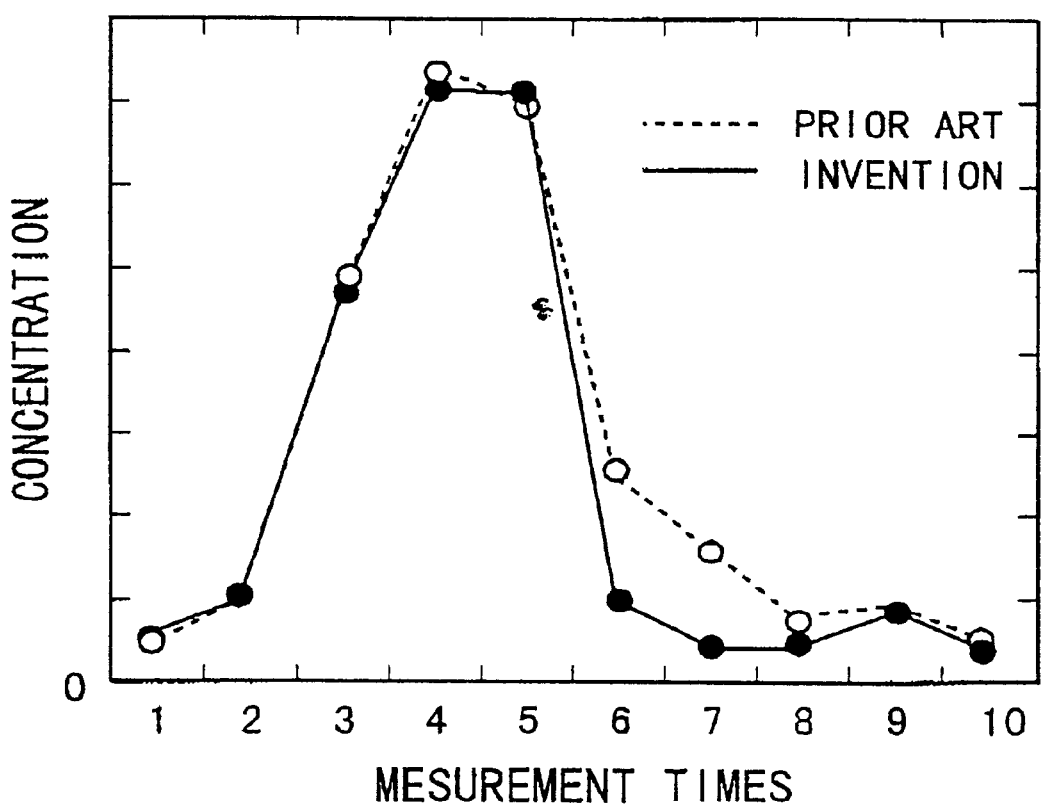
FIG. 16 is a graph showing relationship between the concentration of the desired substance and the measurement times in the apparatus according to the second embodiment of FIG. 14 and the prior-art apparatus of FIG. 1.

FIG. 16 shows the relationship between the concentration of ammonia and the measurement times, in which the solid line denotes the curve obtained in the apparatus according to the second embodiment of FIG. 14, and the broken line denotes the curve obtained in the prior-art apparatus shown in FIG. 1.

As seen from FIG. 16, the concentration of ammonia rises suddenly to a high level from a typical low level in the third to fifth measurement steps and then, it decreases again to the typical low level. In the prior-art apparatus, the concentration is still comparatively high in the sixth to eighth measurement steps, which means that the measured values are not correct. On the other hand, in the apparatus according to the second embodiment of the present invention, the concentration has decreased quickly to the low level in the sixth measurement step, which means that the measured values are correct.

As explained above, with the apparatus according to the second embodiment, the measurement error can be drastically reduced because the cleaner 500 is provided.

In the apparatus according to the second embodiment, two or more samplers and two or more concentrator may be provided, as shown in the apparatus according to the first embodiment. Also, it is needless to say that two or more analyzer and two or more cleaner may be provided as necessary.

Additionally, a reference gas generator for generating a reference gaseous substance in the clean room and a reference gas withdrawer for withdrawing the reference gaseous substance thus generated in the clean room may be added to the configuration of the apparatus according to the first and second embodiments. In this case, calibration of the measured concentration values can be readily performed.

Moreover, in the previously-described first embodiment, if no high-concentration state of the desired substance arises, the cycle time required for each measurement or analysis step is given by the following equation (6).

$$T_{total} = (10 \times T_{sa}) + 2 \times (T_r + T_s) + (T_{pt} - 3 \times T_{sa}) \tag{6}$$

Figure 3:
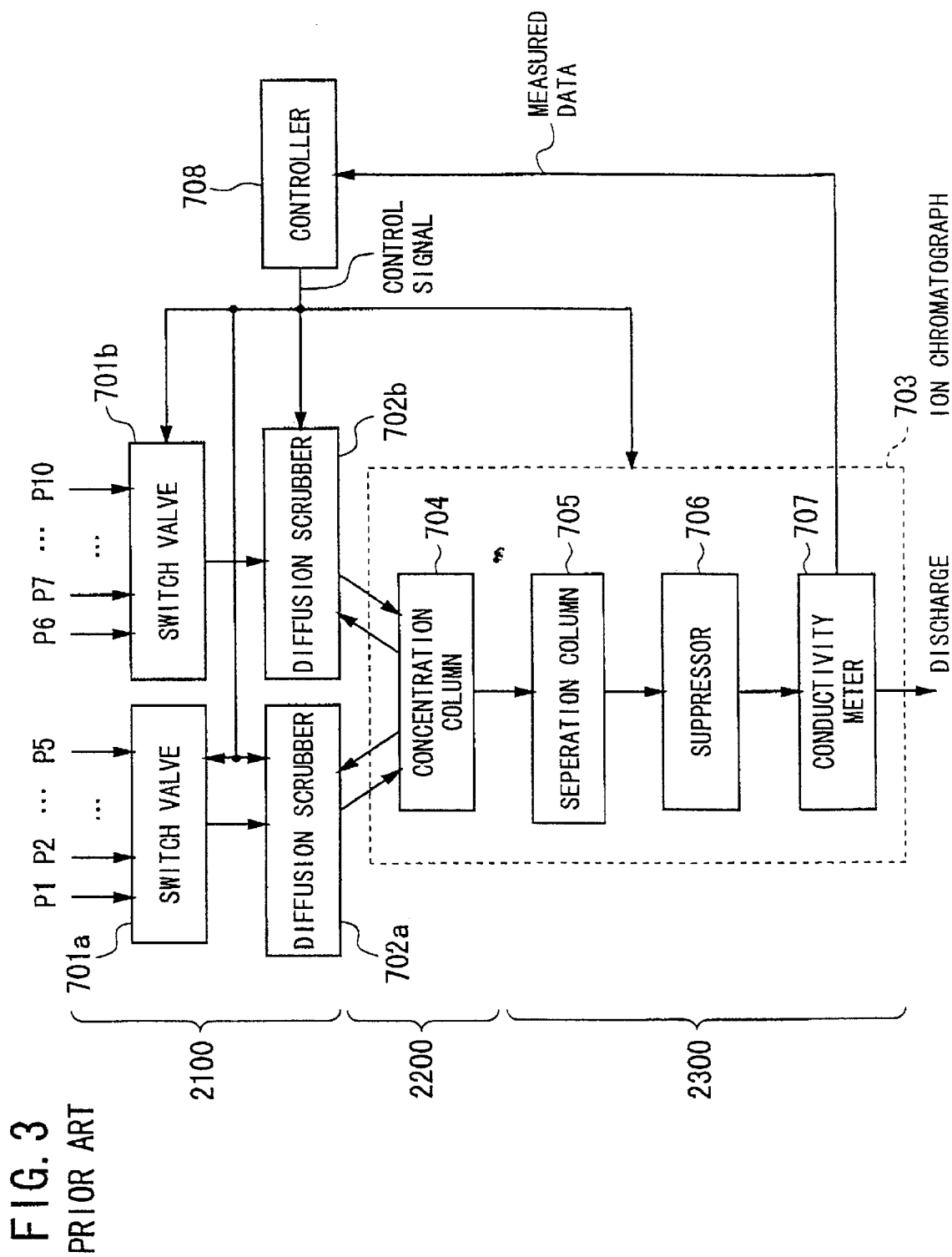
FIG. 3 is a schematic block diagram showing the configuration of another prior-art apparatus for automatically analyzing a trace substance.
Figure 4:
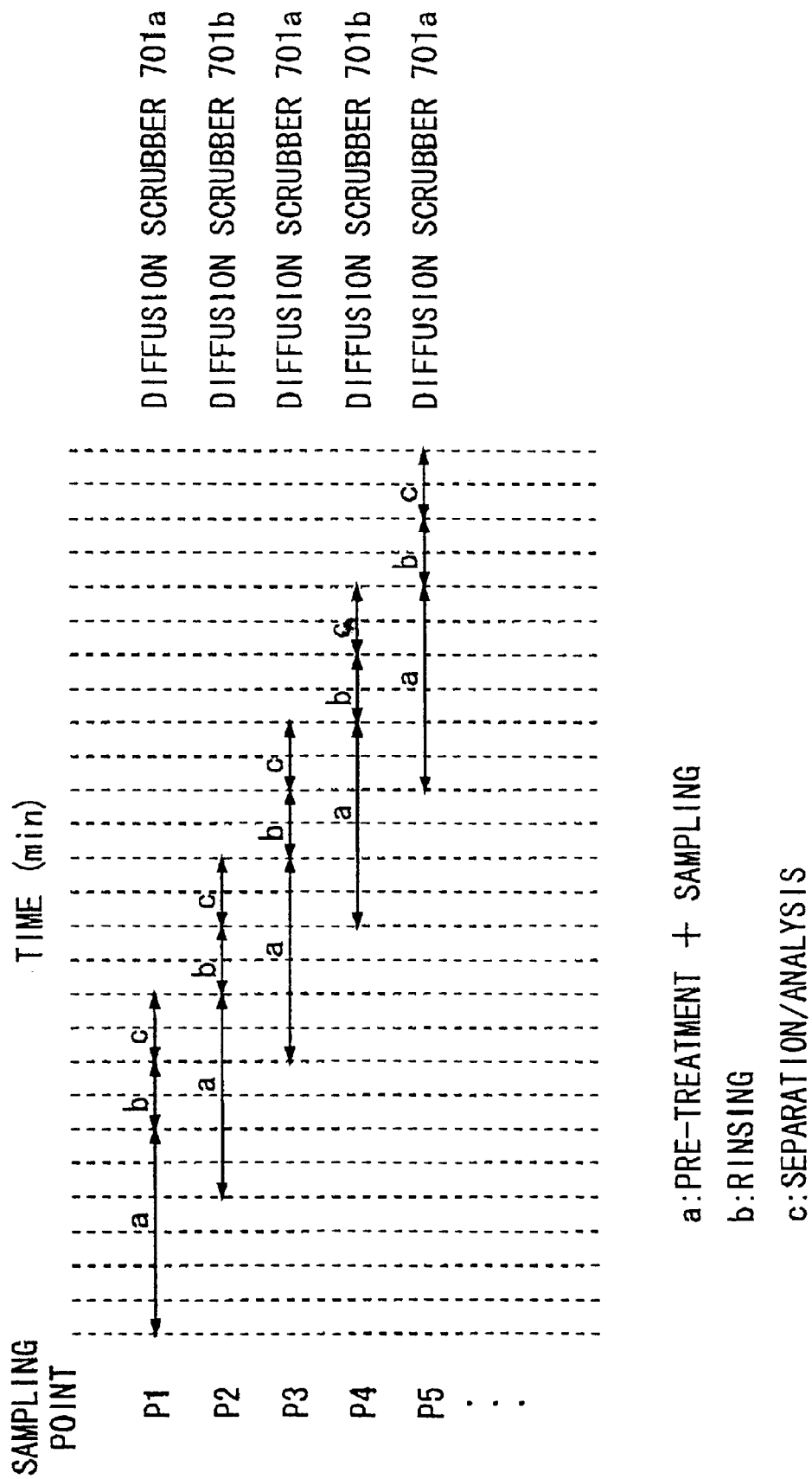
FIG. 4 is a diagram showing the schedule of the individual operations for the ten sampling points in the prior-art apparatus of FIG. 3.

When $T_{pt}=25$ minutes, $T_r=0.5$ minute, $T_s=7.5$ minutes, and $T_{sa}=8$ minutes, the total time $T_{total}$ is 98 minutes, which is much shorter than those of the prior-art apparatuses of FIGS. 1 and 3.

The above equation (6) represents the cycle time while the measuring steps are repeated after the first measurement step. In the first measurement step, the cycle time $T_{total}'$ is given by the following equation (7).

$$T_{total}' = T_{pt} + T_r + T_s + T_{total} \tag{7}$$

While the preferred forms of the present invention have been described, it is to be understood that modifications will be apparent to those skilled in the art without departing from the spirit of the invention. The scope of the invention, therefore, is to be determined solely by the following claims.

What is claimed is:

1. An apparatus for automatically analyzing a trace substance, comprising:
    (a) samplers for making samples at different sampling points, each of said samples containing a desired substance;
    (b) concentrators for concentrating the substance contained in said samples to thereby produce concentrated samples;
    (c) a quantitative analyzer for analyzing quantitatively said substance contained in said concentrated samples; and
    (d) a controller for controlling said samplers, said concentrators and said analyzer to cause automatically operations of said samplers said concentrators, and said analyzer repeatedly at specific intervals of time;
        wherein each of said concentrators receives alternatively one of said samples from one of at least two of said samplers, each group of said at least two of said samplers performing a sampling operation and a separation/analysis operation at nonsimultaneous times, said each group of said at least two of said samplers feeding samples to each of said concentrators;
        and wherein said analyzer receives alternatively one of said concentrated samples from one of said concentrators; at least one of said concentrators not sending concentrated samples to said analyzer being rinsed of residue of a sample previously contained in said at least one concentrator or receiving one of said samples from one of said samplers while said analyzer is receiving said one of said concentrated samples from said one of said concentrators.

2. The apparatus as claimed in claim 1, wherein said desired substance is gaseous and each of said concentrators has a diffusion scrubber and a concentration column.

3. The apparatus as claimed in claim 1, wherein said desired analyzer has a function of ion chromatograph.

4. The apparatus as claimed in claim 1, wherein said controller has a function of monitoring an outbreak of a high-concentration state of said substance.

5. The apparatus as claimed in claim 1, wherein said controller has a function of calculating a cumulative sum of said substance in a specific period of time.

6. The apparatus as claimed in claim 1, further comprising a cleaner for cleaning said samplers by supplying a purging gas into said samplers.

7. The apparatus as claimed in claim 6, wherein said cleaner is comprised of a container for containing said purging gas, and a valve for selecting one of flow paths for said samples and for said purge gas.

8. The apparatus as claimed in claim 6, wherein an analyzing operation comprises;
   (a) a cleaning operation for cleaning said samplers using said purging gas;
   (b) a pre-treatment operation for supplying an absorbing liquid to at least one of said samplers to suppress the effect of a residue of said substance generated in a prior measurement step;
   (c) a rinsing operation for rinsing an eluting liquid remaining in one of said concentrators;
   (d) a sampling operation for making said samples by said samplers and for making said concentrated samples by said concentrators; and
   (e) a separation/analysis operation for separating said substance from said samples and for quantitatively analyzing said separated substance;
       wherein a time of said separation/analysis operation is equal to the sum of a time of said cleaning operation and a time of said pre-treatment operation.

9. The apparatus as claimed in claim 1, wherein each of said diffusion scrubbers has a cleaner for cleaning the same by supplying a purging gas.

10. The apparatus as claimed in claim 1, wherein an analyzing operation comprises;
    (a) a pre-treatment operation for supplying an absorbing liquid to at least one of said samplers to suppress the effect of a residue of said substance generated in a prior measurement step;
    (b) a rinsing operation for rinsing an eluting liquid remaining in one of said concentrators;
    (c) a sampling operation for making said samples by said samplers and for making said concentrated samples by said concentrators; and
    (d) a separation/analysis operation for separating said substance from said samples and for quantitatively analyzing said separated substance;
        wherein a time of said separation/analysis operation is equal to a sum of a time of said rinsing operation and a time of said sampling operation.

11. An apparatus for automatically analyzing a trace substance, comprising:
    (a) samplers for making samples at different sampling points, each of said samples containing a desired substance;
    (b) concentrators for concentrating the substance contained in said samples to thereby produce concentrated samples;
    (c) a quantitative analyzer for analyzing quantitatively said substance contained in said concentrated samples; and
    (d) a controller for controlling said samplers, said concentrators and said analyzer to cause automatically operations of said samplers, said concentrators, and said analyzer repeatedly at specific intervals of time;
        wherein each of said concentrators receives alternatively one of said samples from one of at least two of said samplers;
        wherein said analyzer receives alternatively said concentrated samples from said concentrators; and
        wherein said desired substance is gaseous and each of said concentrators has four diffusion scrubbers and two concentration columns.

12. An apparatus for automatically analyzing a trace substance, comprising:
    (a) samplers for making samples at different sampling points, each of said samples containing a desired substance;
    (b) concentrators for concentrating the substance contained in said samples to thereby produce concentrated samples;
    (c) a quantitative analyzer for analyzing quantitatively said substance contained in said concentrated samples; and
    (d) a controller for controlling said samplers, said concentrators and said analyzer to cause automatically operations of said samplers, said concentrators, and said analyzer repeatedly at specific intervals of time;
        wherein each of said concentrators receives alternatively one of said samples from one of at least two of said samplers;
        wherein said analyzer receives alternatively said concentrated samples from said concentrators; and
        wherein said apparatus further comprises:
    (e) a means for performing a pre-treatment operation for supplying an absorbing liquid to at least one of said samplers to suppress the effect of a residue of said substance generated in a prior measurement step; and
    (f) a means for performing a rinsing operation for rinsing an eluting liquid remaining in one of said concentrators; and wherein said apparatus performs:
        (a) a sampling operation for making said samples by said samplers and for making said concentrated samples by said concentrators; and
        (b) a separation/analysis operation for separating said substance from said samples and for quantitatively analyzing said separated substance by said analyzer;
            wherein a time of said separation/analysis operation is equal to a sum of a time of said rinsing operation and a time of said sampling operation.

13. An apparatus for automatically analyzing a trace substance, comprising:
    (a) samplers for making samples at different sampling points, each of said samples containing a desired substance;
    (b) concentrators for concentrating the substance contained in said samples to thereby produce concentrated samples;
    (c) a quantitative analyzer for analyzing quantitatively said substance contained in said concentrated samples; and
    (d) a controller for controlling said samplers, said concentrators and said analyzer to cause automatically operations of said samplers, said concentrators, and said analyzer repeatedly at specific intervals of time;
        wherein each of said concentrators receives alternatively one of said samples from one of at least two of said samplers;
        wherein said analyzer receives alternatively said concentrated samples from said concentrators; and
        said apparatus further comprising:
    (e) a cleaner for cleaning said samplers by supplying a purging gas into said samplers; and
        wherein said apparatus further comprises:
    (f) a means for performing a pre-treatment operation for supplying an absorbing liquid to at least one of said samplers to suppress the effect of a residue of said substance generated in a prior measurement step; and
    (g) a means for performing a rinsing operation for rinsing an eluting liquid remaining in one of said concentrators; and wherein said apparatus performs:

(a) a sampling operation for making said samples by said samplers and for making said concentrated samples by said concentrators; and (b) a separation/analysis operation for separating said substance from said samples and for quantitatively analyzing said separated substance by said analyzer; wherein a time of said separation/analysis operation is equal to the sum of a time of said cleaning operation and a time of said pre-treatment operation.

14. An apparatus for automatically analyzing a trace substance, comprising:

(a) samplers for making samples at different sampling points, each of said samples containing a desired substance;

(b) concentrators for concentrating the substance contained in said samples to thereby produce concentrated samples;

(c) a quantitative analyzer for analyzing quantitatively said substance contained in said concentrated samples; and (d) a controller for controlling said samplers, said concentrators and said analyzer to cause automatically operations of said samplers, said concentrators, and said analyzer repeatedly at specific intervals of time;

wherein each of said concentrators receives alternatively one of said samples from one of at least two of said samplers;

wherein said analyzer receives alternatively said concentrated samples from said concentrators; and said apparatus further comprising:

(e) a cleaner for cleaning said samplers by supplying a purging gas into said samplers; and wherein said apparatus further comprises:

(f) a means for performing a pre-treatment operation for supplying an absorbing liquid to said samplers to suppress the effect of a residue of said substance generated in a prior measurement step; and (g) a means for performing a rinsing operation for rinsing an eluting liquid remaining in said concentrators;

and wherein said apparatus performs:

(a) a sampling operation for making said samples by said samplers and for making said concentrated samples by said concentrators; and (b) a separation/analysis operation for separating said substance from said sample and for quantitatively analyzing said separated substance by said analyzer;

wherein a time of said separation/analysis operation is equal to the sum of a time of said cleaning operation and a time of said pre-treatment operation.

* * * * *